US010281408B2

(12) United States Patent
Konno et al.

(10) Patent No.: US 10,281,408 B2
(45) Date of Patent: May 7, 2019

(54) INSPECTION OBJECT IMAGING APPARATUS, INSPECTION OBJECT IMAGING METHOD, SURFACE INSPECTION APPARATUS, AND SURFACE INSPECTION METHOD

(71) Applicant: NIPPON STEEL & SUMITOMO METAL CORPORATION, Tokyo (JP)

(72) Inventors: Yusuke Konno, Tokyo (JP); Takamichi Kobayashi, Tokyo (JP); Toshio Akagi, Tokyo (JP); Atsuhiro Hibi, Tokyo (JP); Nobuhiro Furuya, Tokyo (JP); Akihito Nakazaki, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 0 days.

(21) Appl. No.: 15/564,154

(22) PCT Filed: Dec. 19, 2016

(86) PCT No.: PCT/JP2016/087728
§ 371 (c)(1),
(2) Date: Oct. 3, 2017

(87) PCT Pub. No.: WO2017/179243
PCT Pub. Date: Oct. 19, 2017

(65) Prior Publication Data
US 2018/0202941 A1    Jul. 19, 2018

(30) Foreign Application Priority Data

Apr. 12, 2016   (JP) .................................. 2016-079716

(51) Int. Cl.
*G01N 21/88*    (2006.01)
*G01N 21/892*   (2006.01)
(Continued)

(52) U.S. Cl.
CPC ..... *G01N 21/8806* (2013.01); *G01N 21/8851* (2013.01); *G01N 21/892* (2013.01);
(Continued)

(58) Field of Classification Search
CPC ........... G01N 21/8806; G01N 21/8851; G01N 21/94; G01N 21/359; G01N 21/952;
(Continued)

(56) References Cited

U.S. PATENT DOCUMENTS 5,953,115 A  *  9/1999  Landers ............... G01N 21/552
                                                 356/135
6,172,749 B1 *  1/2001  Watanabe .............. G01B 11/30
                                                 257/E21.53
(Continued)

FOREIGN PATENT DOCUMENTS

JP    1-318908 A    12/1989
JP    2000-298102 A    10/2000
(Continued)

OTHER PUBLICATIONS

Beckmann, "Scattering by Composite Rough Surfaces", Proceedings of the IEEE, 1965, vol. 53, Issue 8, pp. 1012-1015.
(Continued)

*Primary Examiner* — Taeho Jo
(74) *Attorney, Agent, or Firm* — Birch, Stewart, Kolasch & Birch, LLP

(57) ABSTRACT

An inspection object imaging apparatus includes: a light source configured to produce a light beam belonging to an infrared wavelength band and having a predetermined spread half-angle on a surface of an inspection object; a projection optical system to project the light beam on the surface of the inspection object at a predetermined projection angle; and an imaging unit. The imaging unit includes an imaging optical system configured to condense reflected
(Continued)

light and branch the reflected light to two different directions, and a first image sensor and a second image sensor, the first image sensor positioned on the inspection object side with respect to a position of the imaging optical system that is conjugate with the surface of the inspection object, along an optical axis of the reflected light, and the second image sensor positioned on the reflected-light travel direction side with respect to the conjugate position.

24 Claims, 24 Drawing Sheets

(51) Int. Cl.
- *G01N 21/94* (2006.01)
- *G01N 21/952* (2006.01)
- *G01N 21/359* (2014.01)
- *G01N 21/00* (2006.01)
- *G01N 15/06* (2006.01)

(52) U.S. Cl.
CPC ............ *G01N 15/06* (2013.01); *G01N 21/00* (2013.01); *G01N 21/359* (2013.01); *G01N 21/88* (2013.01); *G01N 21/94* (2013.01); *G01N 21/952* (2013.01); *G01N 2201/0697* (2013.01)

(58) Field of Classification Search
CPC .............. G01N 21/00; G01N 21/892; G01N 2201/0697; G01N 15/06; G01N 21/88
USPC ...................................................... 250/338.1
See application file for complete search history.

(56) References Cited

U.S. PATENT DOCUMENTS

| | | | | |
|---|---|---|---|---|
| 9,404,854 | B2* | 8/2016 | Hunt | G01N 21/3581 |
| 2004/0119018 | A1* | 6/2004 | Alfano | G01N 21/8806 |
| | | | | 250/341.1 |
| 2006/0001864 | A1* | 1/2006 | Kanzaki | G01N 21/94 |
| | | | | 356/237.2 |
| 2008/0317090 | A1* | 12/2008 | Tralshawala | G01N 25/72 |
| | | | | 374/43 |
| 2009/0097033 | A1* | 4/2009 | Kuusela | G01N 21/57 |
| | | | | 356/446 |
| 2009/0245622 | A1* | 10/2009 | Janin | G01N 21/8901 |
| | | | | 382/152 |
| 2011/0043798 | A1* | 2/2011 | Markwort | G01N 21/9501 |
| | | | | 356/237.5 |
| 2011/0181873 | A1* | 7/2011 | Yavets-Chen | G01N 21/55 |
| | | | | 356/237.2 |
| 2013/0320216 | A1* | 12/2013 | Aiko | G01B 11/303 |
| | | | | 250/349 |
| 2013/0322479 | A1 | 12/2013 | Sugiyama et al. | |
| 2013/0342880 | A1* | 12/2013 | Ciardullo | H04N 1/00588 |
| | | | | 358/496 |
| 2014/0022379 | A1* | 1/2014 | Ohama | B41F 33/0036 |
| | | | | 348/125 |
| 2016/0076942 | A1* | 3/2016 | Zawaideh | G01J 4/04 |
| | | | | 356/364 |
| 2016/0116400 | A1* | 4/2016 | Hunt | G01N 21/3581 |
| | | | | 250/341.1 |
| 2016/0209325 | A1* | 7/2016 | Kotidis | B82Y 20/00 |
| 2017/0146463 | A1* | 5/2017 | Honda | G01N 21/9501 |
| 2017/0191946 | A1* | 7/2017 | Smith | G01N 21/8901 |

FOREIGN PATENT DOCUMENTS

| | | |
|---|---|---|
| JP | 2001-242090 A | 9/2001 |
| JP | 2002-139447 A | 5/2002 |
| JP | 2007-327896 A | 12/2007 |
| JP | 2008-157788 A | 7/2008 |
| JP | 2009-80033 A | 4/2009 |
| JP | 2010-133967 A | 6/2010 |
| JP | 2012-13614 A | 1/2012 |
| JP | 2013-254764 A | 12/2013 |

OTHER PUBLICATIONS

International Search Report for PCT/JP2016/087728 (PCT/ISA/210) dated Mar. 7, 2017.
Written Opinion of the International Searching Authority for PCT/JP2016/087728 (PCT/ISA/237) dated Mar. 7, 2017.
Japanese Office Action, dated May 15, 2018, for Japanese Application No. 2017-526987, with a partial translation.
Extended European Search Report, dated Jan. 22, 2019 for corresponding European Application No. 16897469.9.
Korean Office Action, dated Jan. 28, 2019, for corresponding Korean Application No. 10-2017-7030929, with a partial English translation.

* cited by examiner

FIG. 6
| CO2 LASER LIGHT SOURCE | QUANTUM CASCADE LASER LIGHT SOURCE |
|---|---|
| CENTER WAVELENGTH: 10.6 μm<br>SPECTRAL BANDWIDTH : 1 nm | CENTER WAVELENGTH: 10 μm<br>SPECTRAL BANDWIDTH : 400 nm |
| 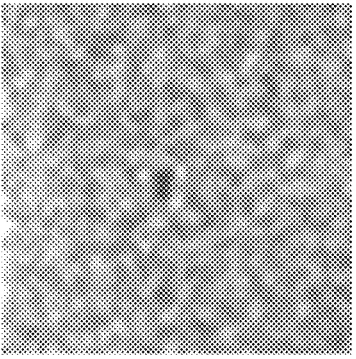 | 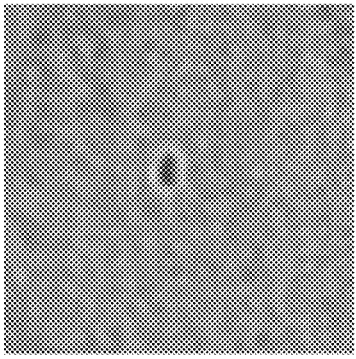 |

FIG. 13
WHEN VIEWED IN AXIAL DIRECTION
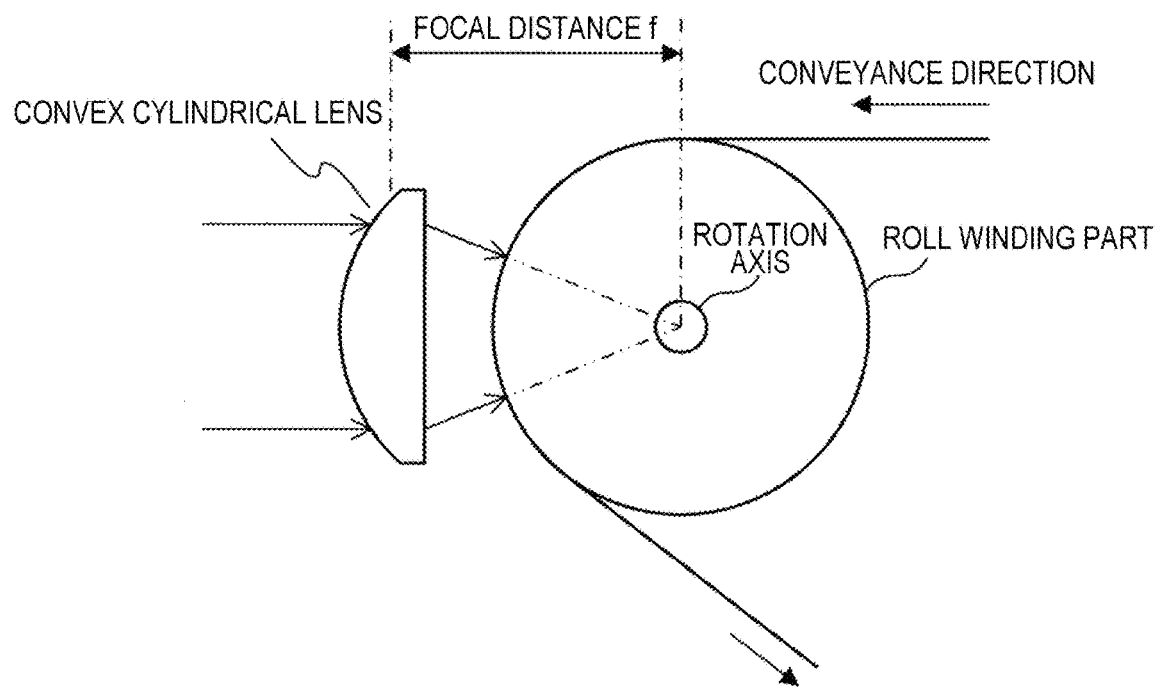
WHEN VIEWED FROM ABOVE
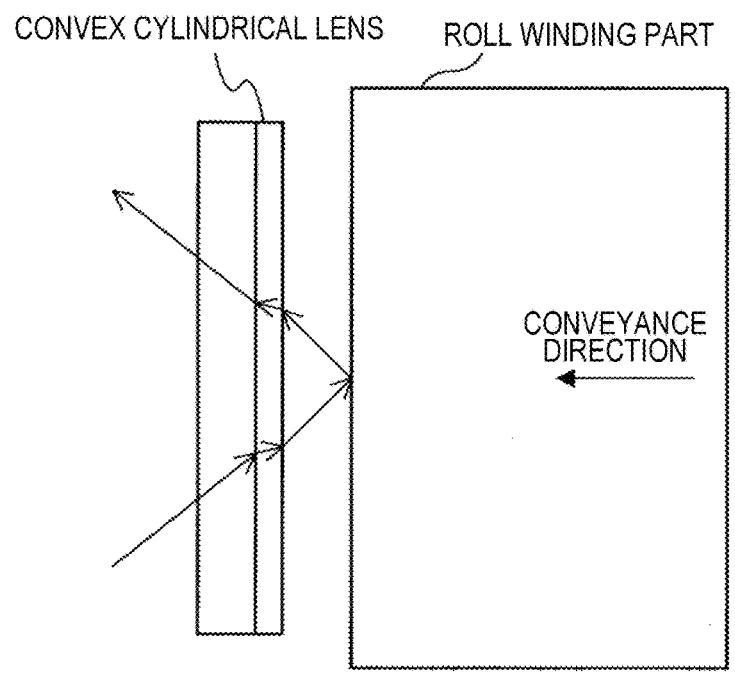

FIG. 20
Δ = −3 mm
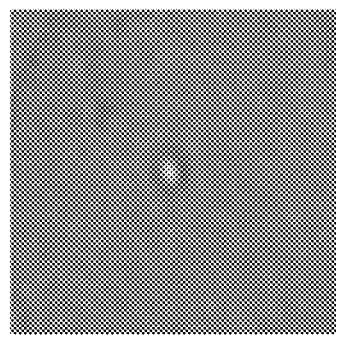
Δ = 3 mm
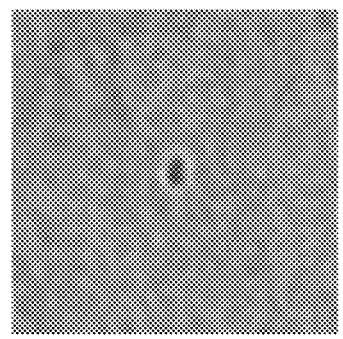

INSPECTION OBJECT IMAGING APPARATUS, INSPECTION OBJECT IMAGING METHOD, SURFACE INSPECTION APPARATUS, AND SURFACE INSPECTION METHOD

TECHNICAL FIELD

The present invention relates to an inspection object imaging apparatus, an inspection object imaging method, a surface inspection apparatus, and a surface inspection method.

BACKGROUND ART

For example, in producing a metal plate, such as a cold-rolled steel sheet, a process of rolling an intermediate product (e.g., a hot-rolled steel sheet) is performed. In such a rolling process, stretching is performed using a rolling mill roll so that the final product has a desired thickness. In the case where a foreign substance is attached to the rolling mill roll, the foreign substance may cause an unevenness flaw on the surface of the metal plate. In the case where the rolling mill roll is under micro vibration, the vibration may cause fine lateral stripes (chatter marks) to be formed on the surface of the metal plate. Furthermore, dirt on a production line or the like may cause harmless dirt to be attached to the surface of the metal plate.

The amount of unevenness of this unevenness flaw is from approximately 1 μm to approximately 10 times larger than that. On the other hand, the surface of a steel strip in a production process before coating has a roughness of approximately 0.5 μm to 1 μm, which is comparable to visible light; thus, a diffuse reflection component is large in visual inspection by visible light, and it is difficult to find unevenness defects. To detect such unevenness defects, conventionally, visual inspection has been performed after honing had been performed on a metal plate by an inspector. When honing is performed on a metal plate, a convexity is polished further than a concavity to become closer to a specular surface, whereas the concavity remains as the original rough surface; thus, a part with unevenness becomes clear to be visually checkable. However, there has been a problem in that time and effort are taken for visually checking presence or absence of an unevenness flaw on a produced metal plate.

To solve such problems, studies have been carried out for a method of detecting micro defects present on the surface of a steel sheet without visual check, by using light belonging to the infrared wavelength band (infrared light). For example, Patent Literature 1 below discloses a method of detecting micro unevenness flaws present on the surface of an inspection target by applying infrared light to the inspection target, projecting reflected light from the inspection target on a screen, and observing light and dark with a camera. In addition, Patent Literature 2 below discloses a method of applying infrared laser light made into divergent light to an inspection object, and imaging, with a camera, reflected light from the inspection object condensed by a concave mirror.

CITATION LIST

Patent Literature

Patent Literature 1: JP 2010-133967A
Patent Literature 2: JP 2009-80033A

Non-Patent Literature

Non-Patent Literature 1: P. Beckmann, "Scattering by composite rough surfaces", Proceedings of the IEEE, Vol. 53, Issue 8 (1965), 1012-1015.

SUMMARY OF INVENTION

Technical Problem

However, in regard to the method of Patent Literature 1, there has been a problem of difficulty in distinguishing between dirt and an unevenness flaw, because the light-and-dark pattern of the camera does not necessarily coincide with unevenness of the flaw. There has also been a problem in that in the case where a laser is used for illumination, speckle noise appears when reflected light is projected on the screen, which is a diffusing surface, and accurate inspection cannot be performed. Furthermore, there has been a problem in that, in this method, a light source needs power for favorable observation of light and dark, because only part of light scattered at the screen enters the camera.

Moreover, in regard to the method of Patent Literature 2, it is difficult to greatly change the angle of an optical axis from 180 degrees with a concave mirror, which results in presence of a region where optical paths overlap; thus, there has been a problem of difficulty in reducing the size of an apparatus. There has also been a problem in that the size of the concave mirror is inevitably larger than an inspection range, which also poses difficulty in reducing the size of an apparatus.

Hence, the present invention is made in view of the above problems, and an object of the present invention is to provide an inspection object imaging apparatus, an inspection object imaging method, a surface inspection apparatus, and a surface inspection method that are capable of detecting, with high sensitivity, an unevenness defect or the like that has occurred on the surface of an inspection object having a surface roughness comparable to wavelengths of visible light and is comparable to several times the surface roughness, and accurately distinguishing between dirt and an unevenness flaw present on the surface of the inspection object, and that also enable a reduction in the size of an apparatus.

Solution to Problem

According to an aspect of the present invention in order to achieve the above-mentioned object, there is provided an inspection object imaging apparatus including: a light source configured to produce a light beam belonging to an infrared wavelength band, a spread half-angle of the light beam on a surface of an inspection object being 20 times or less a minimum inclination of a surface to be imaged; a projection optical system configured to project the light beam on the surface of the inspection object at a predetermined projection angle; and an imaging unit configured to image the light beam reflected at the surface of the inspection object. The imaging unit includes an imaging optical system including at least one convex lens, configured to condense reflected light from the surface of the inspection object, and including a branching optical element that branches the reflected light to two different directions, and a first image sensor and a second image sensor each configured to image the reflected light that has passed through the imaging optical system. The first image sensor is provided on the inspection object side with respect to a position of the imaging optical system that is conjugate with the surface of the inspection object, along an optical axis of the reflected light. The second image sensor is provided on the reflected-light travel direction side with respect to the conjugate position of the imaging optical system, along an optical axis of the reflected light.

According to another aspect of the present invention in order to achieve the above-mentioned object, there is provided an inspection object imaging method including: projecting, from a light source configured to produce a light beam belonging to an infrared wavelength band, a spread half-angle of the light beam on a surface of an inspection object being 20 times or less a minimum inclination of a surface to be imaged, the light beam on the surface of the inspection object at a predetermined projection angle via a projection optical system; condensing reflected light that is the light beam reflected at the surface of the inspection object using an imaging optical system including at least one convex lens, and branching the reflected light to two different directions by a branching optical element included in the imaging optical system; and imaging the reflected light that has formed an image in a first image sensor, by the first image sensor provided on the inspection object side with respect to a position of the imaging optical system that is conjugate with the surface of the inspection object, along an optical axis of the reflected light, and imaging the reflected light that has formed an image in a second image sensor, by the second image sensor provided on the reflected-light travel direction side with respect to the conjugate position of the imaging optical system, along an optical axis of the reflected light.

The imaging optical system may further include a first condensing optical system provided between the branching optical element and the first image sensor, and configured to condense the reflected light onto the first image sensor, and a second condensing optical system provided between the branching optical element and the second image sensor, and configured to condense the reflected light onto the second image sensor.

The light beam produced by the light source may be parallel light.

For each of the first image sensor and the second image sensor, a shift amount Δ [mm] from the conjugate position may be set to satisfy a condition expressed by Formula (1) below, where β is a lateral magnification of the imaging optical system, p [mm] is a pixel pitch in each image sensor, and T is a minimum value of an inclination to be imaged on the surface.

The light source may be a quantum cascade laser without an external resonator.

The inspection object may be positioned on a surface of a roll having a predetermined curvature. The projection optical system and the imaging optical system may include a cylindrical lens whose focus coincides with a rotation center axis of the roll.

The first image sensor and the second image sensor may be provided to be inclined with respect to an optical axis so that a shift amount from the conjugate position at pixel positions in each image sensor is constant.

[Math. 1]

$$\Delta > \frac{p \cdot \beta}{T} \quad \text{Formula (1)}$$

According to still another aspect of the present invention in order to achieve the above-mentioned object, there is provided a surface inspection apparatus including: an inspection object imaging apparatus that projects a light beam belonging to an infrared wavelength band on a surface of an inspection object at a predetermined projection angle, and images reflected light from the surface of the inspection object; and an arithmetic processing apparatus that performs image processing on captured images of the reflected light captured by the inspection object imaging apparatus, and detects a surface defect present on the surface of the inspection object, the inspection object imaging apparatus including a light source configured to produce a light beam belonging to an infrared wavelength band, a spread half-angle of the light beam on a surface of an inspection object being 20 times or less a minimum inclination of a surface to be imaged, a projection optical system configured to project the light beam on the surface of the inspection object at a predetermined projection angle, and an imaging unit configured to image the light beam reflected at the surface of the inspection object. The imaging unit includes an imaging optical system including at least one convex lens, configured to condense reflected light from the surface of the inspection object, and including a branching optical element that branches the reflected light to two different directions, and a first image sensor and a second image sensor each configured to image the reflected light that has passed through the imaging optical system. The first image sensor is provided on the inspection object side with respect to a position of the imaging optical system that is conjugate with the surface of the inspection object, along an optical axis of the reflected light. The second image sensor is provided on the reflected-light travel direction side with respect to the conjugate position of the imaging optical system, along an optical axis of the reflected light. On the basis of distribution of light and dark of a first captured image captured by the first image sensor and a second captured image captured by the second image sensor, the arithmetic processing apparatus detects a portion where light and dark are reversed between the first captured image and the second captured image, as unevenness present on the surface of the inspection object.

According to still another aspect of the present invention in order to achieve the above-mentioned object, there is provided a surface inspection method including: a step of projecting, from a light source configured to produce a light beam belonging to an infrared wavelength band, a spread half-angle of the light beam on a surface of an inspection object being 20 times or less a minimum inclination of a surface to be imaged, the light beam on the surface of the inspection object at a predetermined projection angle via a projection optical system, condensing reflected light that is the light beam reflected at the surface of the inspection object using an imaging optical system including at least one convex lens, and branching the reflected light to two different directions by a branching optical element included in the imaging optical system, and imaging the reflected light that has formed an image in a first image sensor, by the first image sensor provided on the inspection object side with respect to a position of the imaging optical system that is conjugate with the surface of the inspection object, along an optical axis of the reflected light, and imaging the reflected light that has formed an image in a second image sensor, by the second image sensor provided on the reflected-light travel direction side with respect to the conjugate position of the imaging optical system, along an optical axis of the reflected light; and a step of, on the basis of distribution of light and dark of a first captured image captured by the first image sensor and a second captured image captured by the second image sensor, detecting a portion where light and dark are reversed between the first captured image and the second captured image, as unevenness present on the surface of the inspection object.

The imaging optical system may further include a first condensing optical system provided between the branching optical element and the first image sensor, and configured to condense the reflected light onto the first image sensor, and a second condensing optical system provided between the branching optical element and the second image sensor, and configured to condense the reflected light onto the second image sensor.

The light beam produced by the light source may be parallel light.

For each of the first image sensor and the second image sensor, a shift amount $\Delta$ [mm] from the conjugate position may be set to satisfy a condition expressed by Formula (1) below, where $\beta$ is a lateral magnification of the imaging optical system, p [mm] is a pixel pitch in each image sensor, and T is a minimum value of an inclination to be detected on the surface.

The light source may be a quantum cascade laser without an external resonator.

The inspection object may be positioned on a surface of a roll having a predetermined curvature. The projection optical system and the imaging optical system may include a cylindrical lens whose focus coincides with a rotation center axis of the roll.

The first image sensor and the second image sensor may be provided to be inclined with respect to an optical axis so that a shift amount from the conjugate position at pixel positions in each image sensor is constant.

[Math. 2]

$$\Delta > \frac{p \cdot \beta}{T} \quad \text{Formula (1)}$$

Advantageous Effects of Invention

As described above, according to the present invention, reflected light from the surface of an inspection object is condensed by an optical element including at least one convex lens, and the reflected light is imaged by two image sensors provided to be shifted from a position conjugate with the surface of the inspection object; thus, an apparatus can be reduced in size, and an unevenness defect or the like that has occurred on the surface of an inspection object having a surface roughness comparable to wavelengths of visible light and is comparable to several times the surface roughness can be detected with high sensitivity. In addition, by using captured images generated by the two image sensors, it is possible to accurately distinguish between dirt and an unevenness flaw present on the surface of a metal plate.

BRIEF DESCRIPTION OF DRAWINGS

FIG. 6 is an explanatory diagram for describing a light source of an inspection object imaging apparatus according to the embodiment.

FIG. 13 is an explanatory diagram for describing an example of a light beam projecting unit and an imaging optical system of an inspection object imaging apparatus according to the embodiment.

FIG. 20 is an explanatory diagram showing imaging results of a metal surface obtained by an inspection object imaging apparatus according to the embodiment.

DESCRIPTION OF EMBODIMENTS

Figure 1:
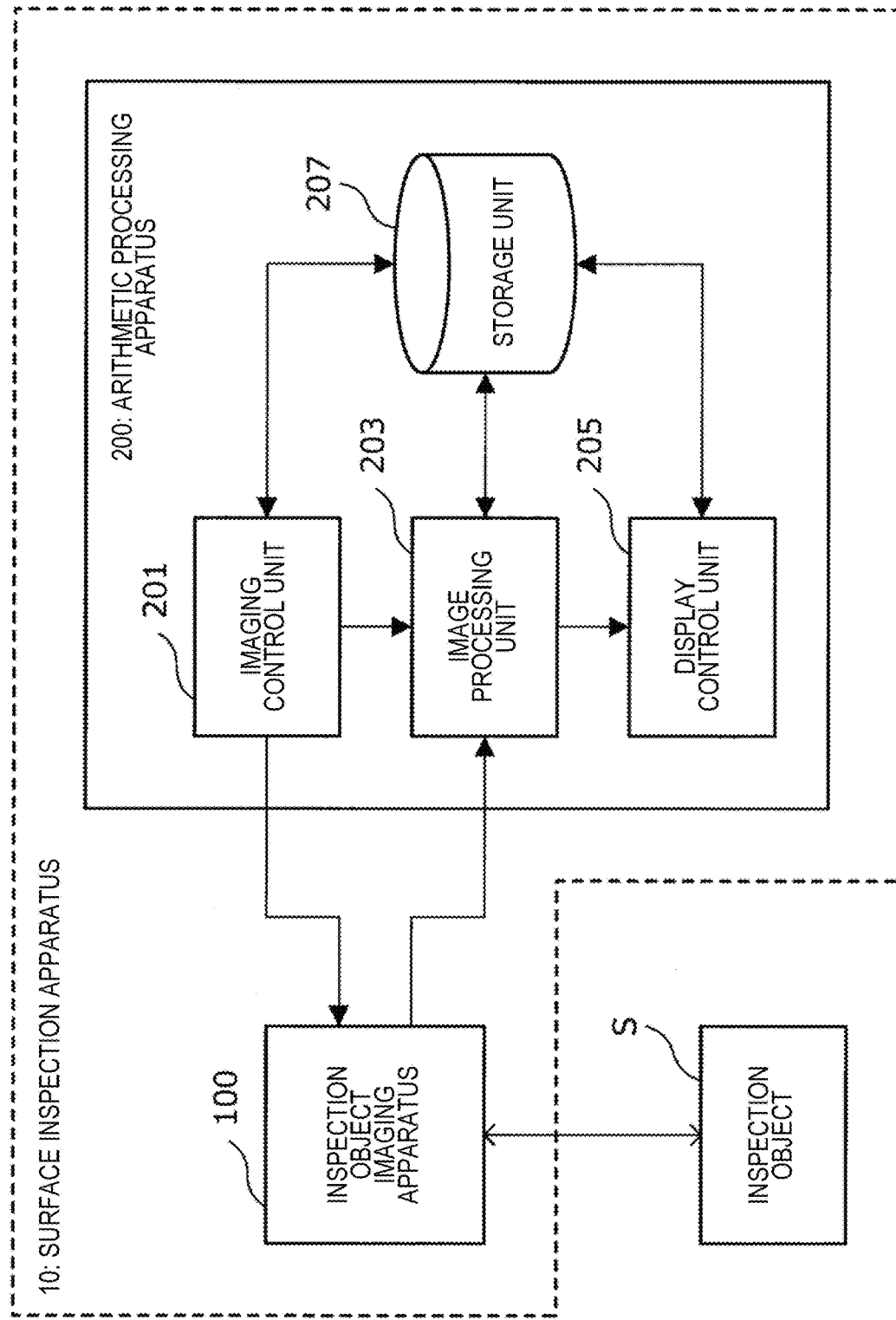
FIG. 1 is an explanatory diagram illustrating a surface inspection apparatus according to an embodiment of the present invention.

Hereinafter, (a) preferred embodiment(s) of the present invention will be described in detail with reference to the appended drawings. In this specification and the appended drawings, structural elements that have substantially the same function and structure are denoted with the same reference numerals, and repeated explanation of these structural elements is omitted.

<Configuration of Surface Inspection Apparatus>

First, a configuration of a surface inspection apparatus according to an embodiment of the present invention is described with reference to FIG. 1. FIG. 1 is an explanatory diagram illustrating a configuration of a surface inspection apparatus 10 according to the present embodiment.

The surface inspection apparatus 10 according to the present embodiment mainly includes an inspection object imaging apparatus 100 and an arithmetic processing apparatus 200, as illustrated in FIG. 1.

The inspection object imaging apparatus 100 projects a light beam belonging to the infrared wavelength band and having a predetermined spread half-angle, which is described in detail later, on an inspection object S, and images reflected light of the light beam from the surface of the inspection object S to generate a captured image of the surface of the inspection object S. The captured image of the surface of the inspection object S generated by the inspection object imaging apparatus 100 is output to the arithmetic processing apparatus 200.

The arithmetic processing apparatus 200 performs image processing on the captured image generated by the inspection object imaging apparatus 100, and detects a surface defect (in particular, an unevenness flaw) present on the surface of the inspection object S.

The inspection object imaging apparatus 100 and the arithmetic processing apparatus 200 are described below in detail.

The inspection object S according to the present embodiment may be a metal plate capable of reflecting a light beam belonging to the infrared wavelength band that is projected from the inspection object imaging apparatus 100. The inspection object S is not particularly limited, and examples include various steel sheets including alloys, and so-called nonferrous metal plates.

<Configuration of Inspection Object Imaging Apparatus>

Now, a configuration of the inspection object imaging apparatus 100 according to the present embodiment will be described in detail with reference to FIGS. 2 to 13.

Figure 2:
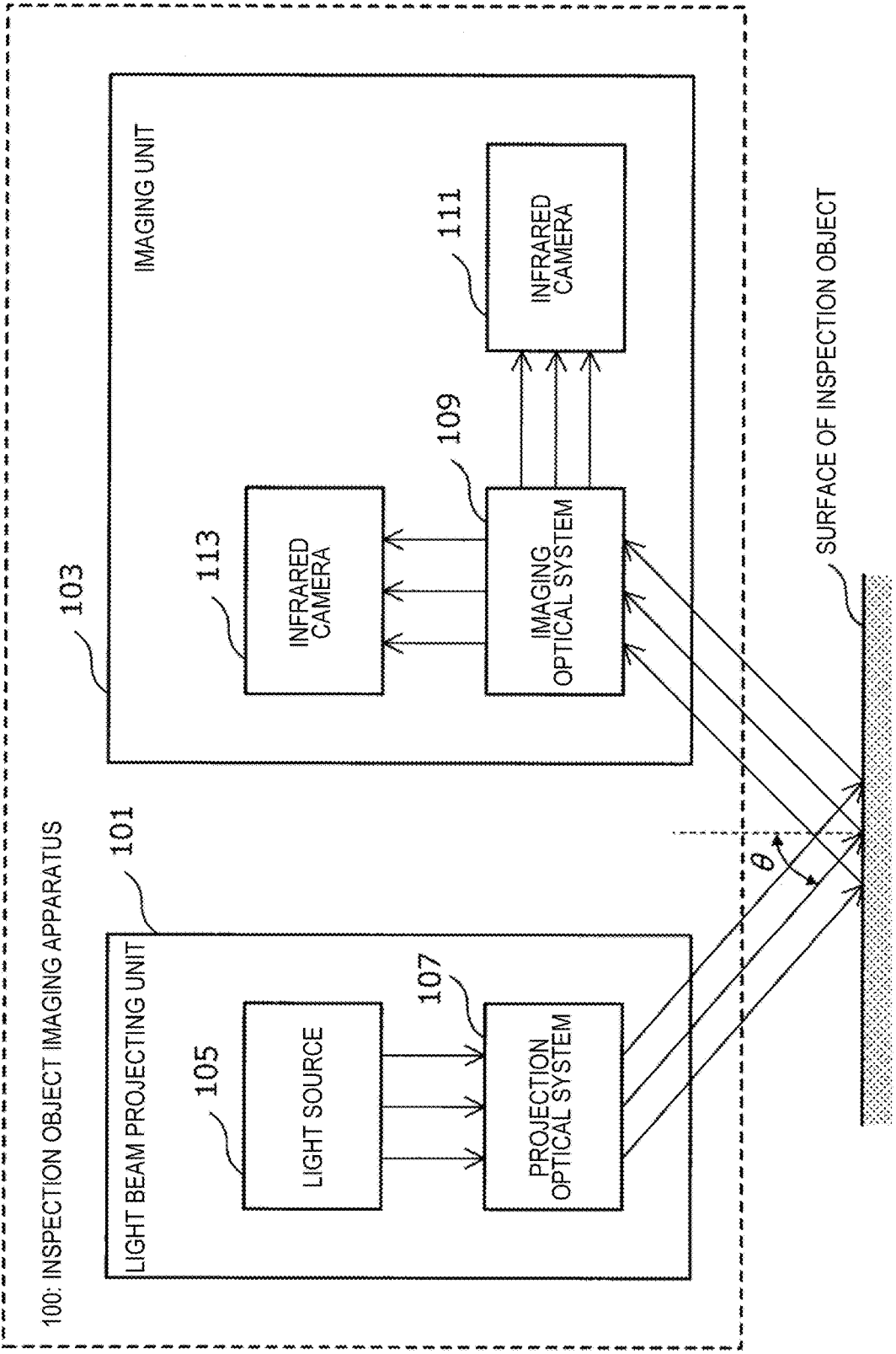
FIG. 2 is an explanatory diagram illustrating an inspection object imaging apparatus according to the embodiment.
Figure 7:
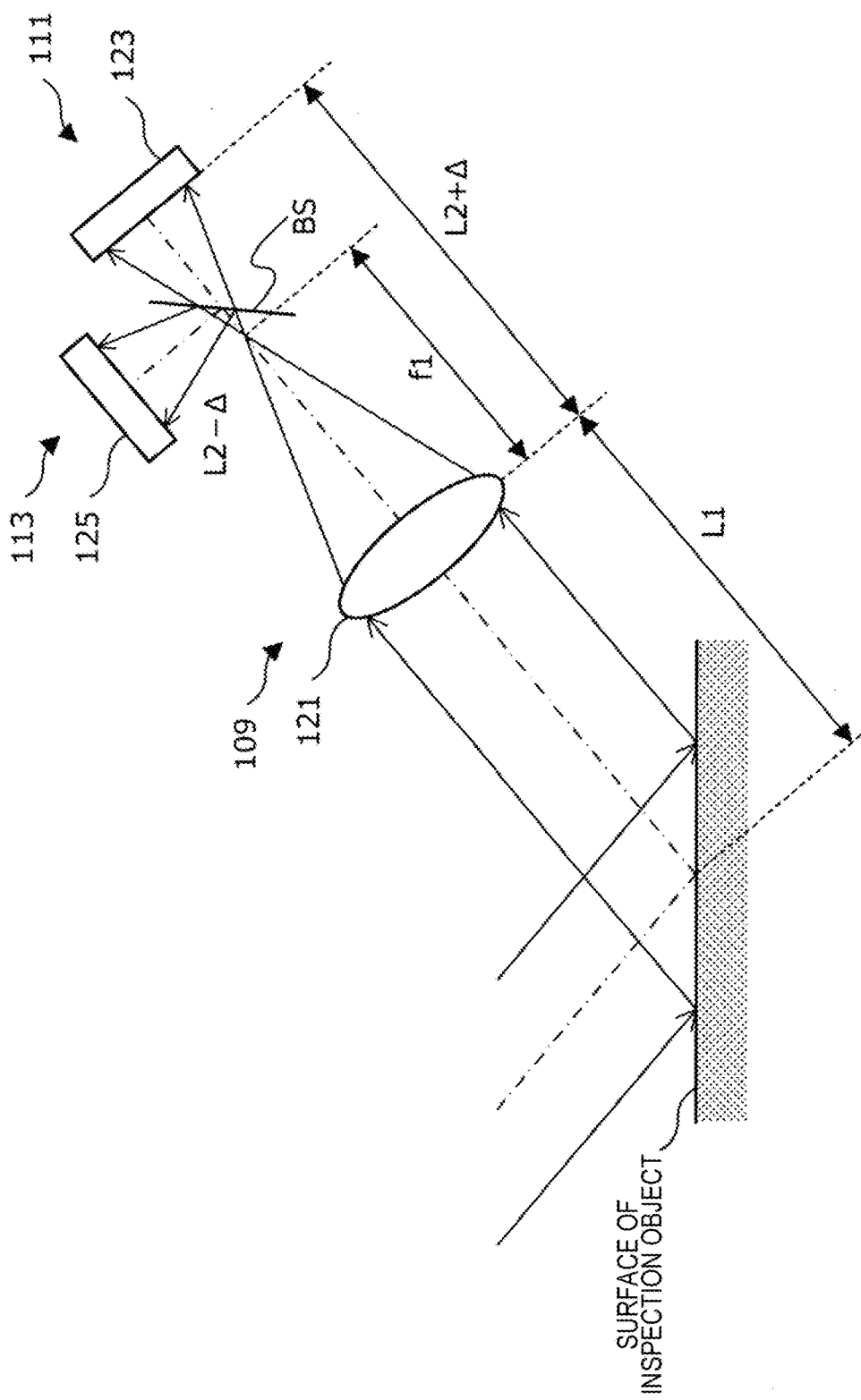
FIG. 7 is an explanatory diagram illustrating an example of an imaging unit of an inspection object imaging apparatus according to the embodiment.
Figure 8:
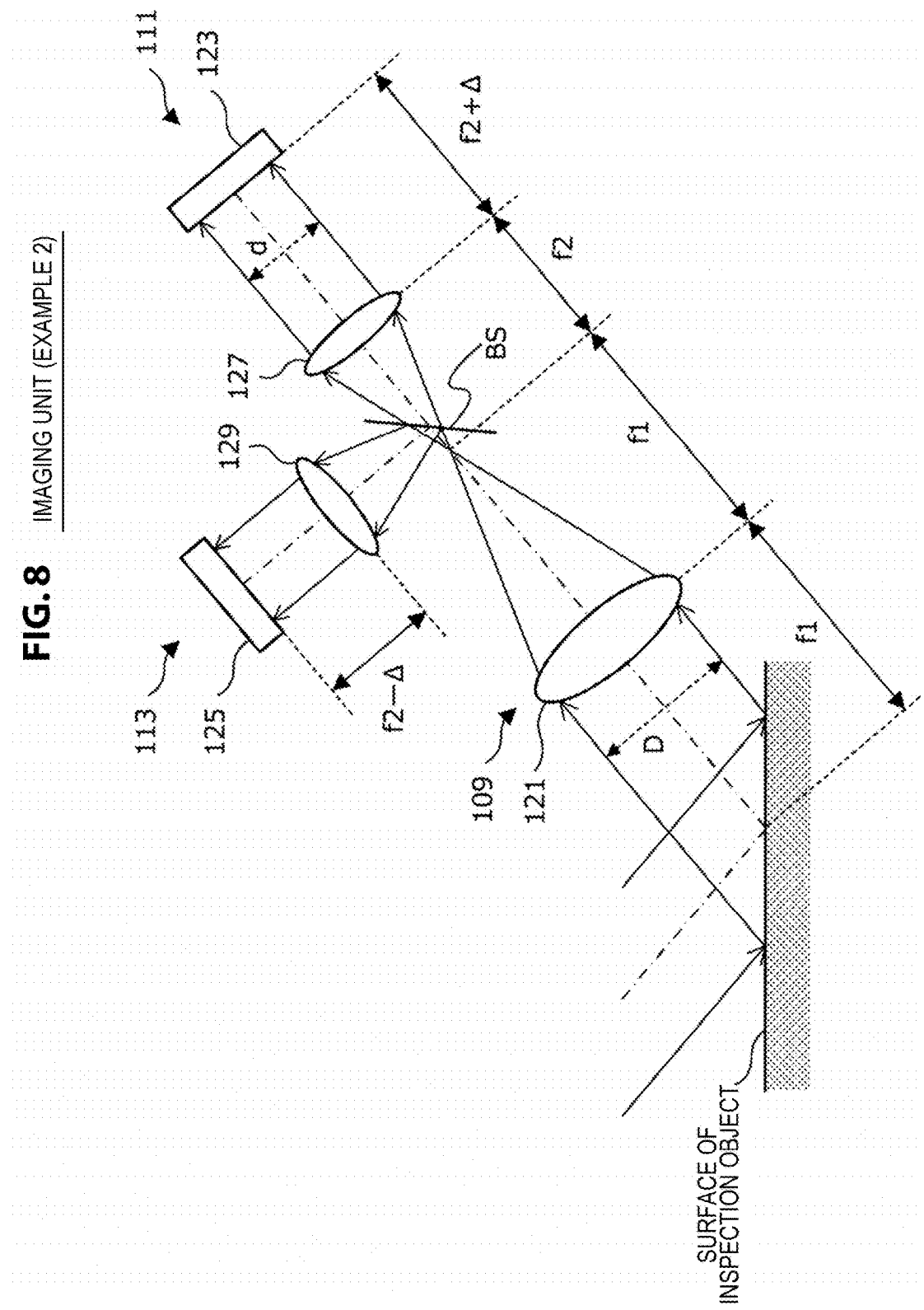
FIG. 8 is an explanatory diagram illustrating an example of an imaging unit of an inspection object imaging apparatus according to the embodiment.
Figure 9:
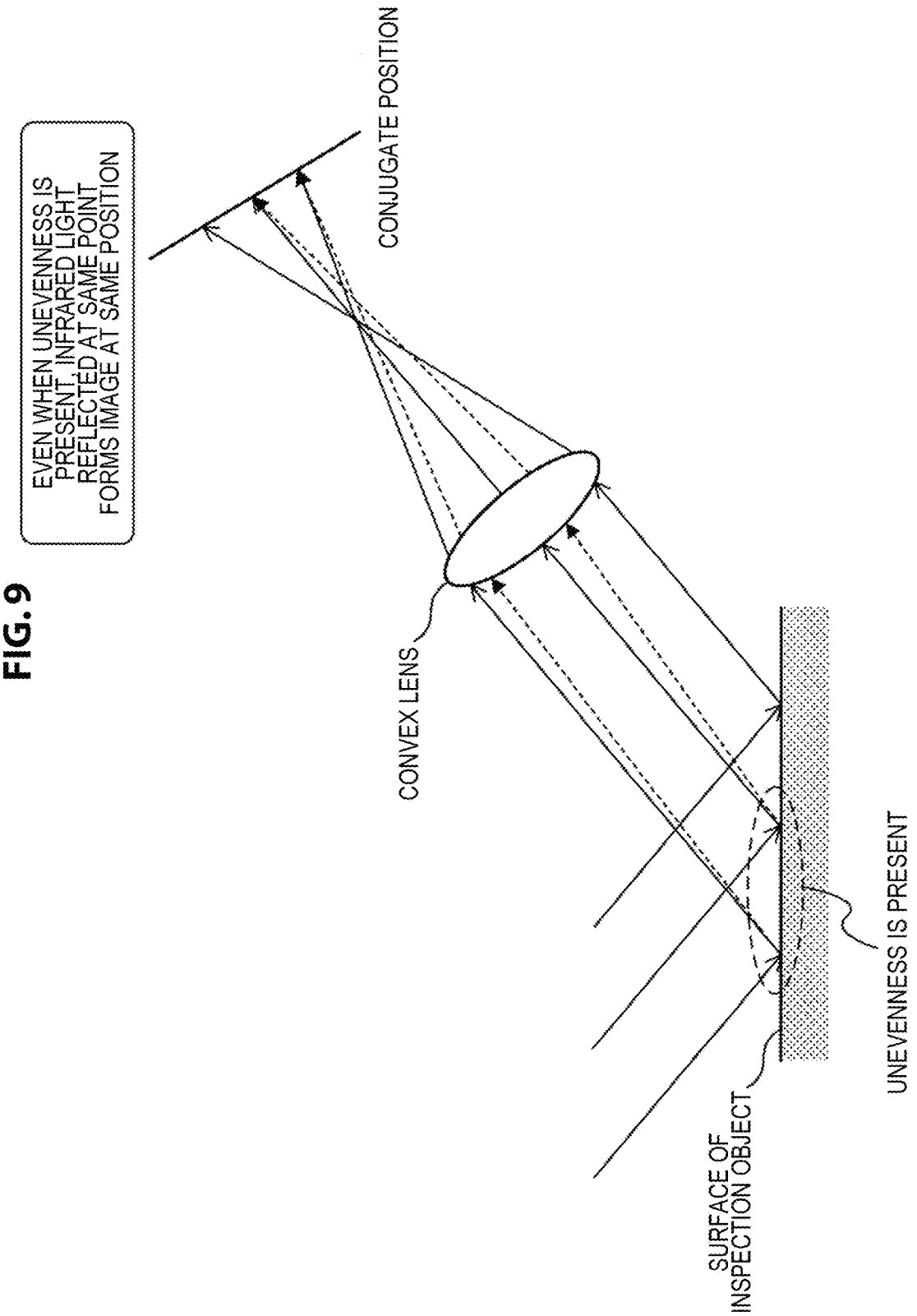
FIG. 9 is an explanatory diagram for describing how an image is formed at a conjugate position.
Figure 10:
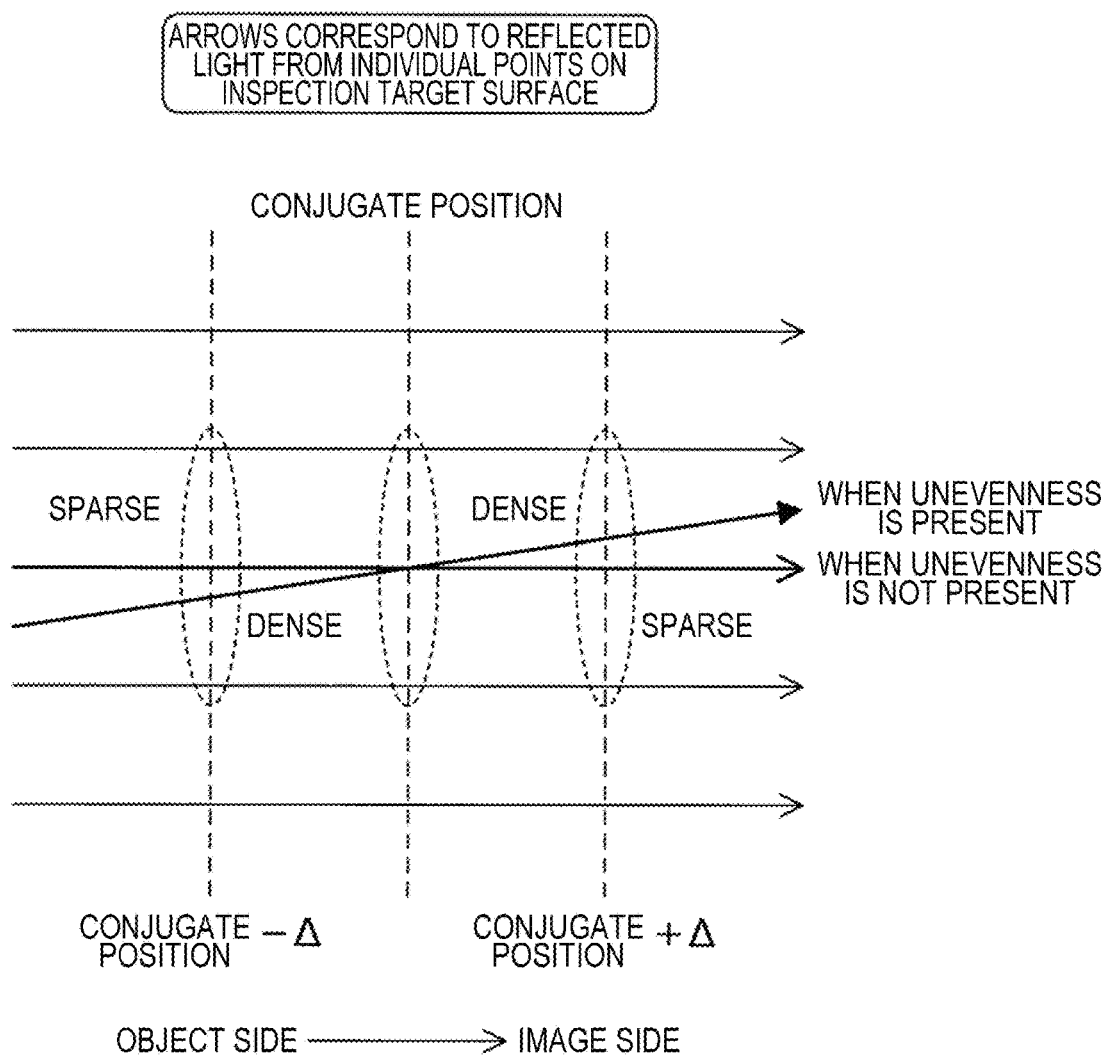
FIG. 10 is an explanatory diagram for describing an imaging unit of an inspection object imaging apparatus according to the embodiment.
Figure 11:
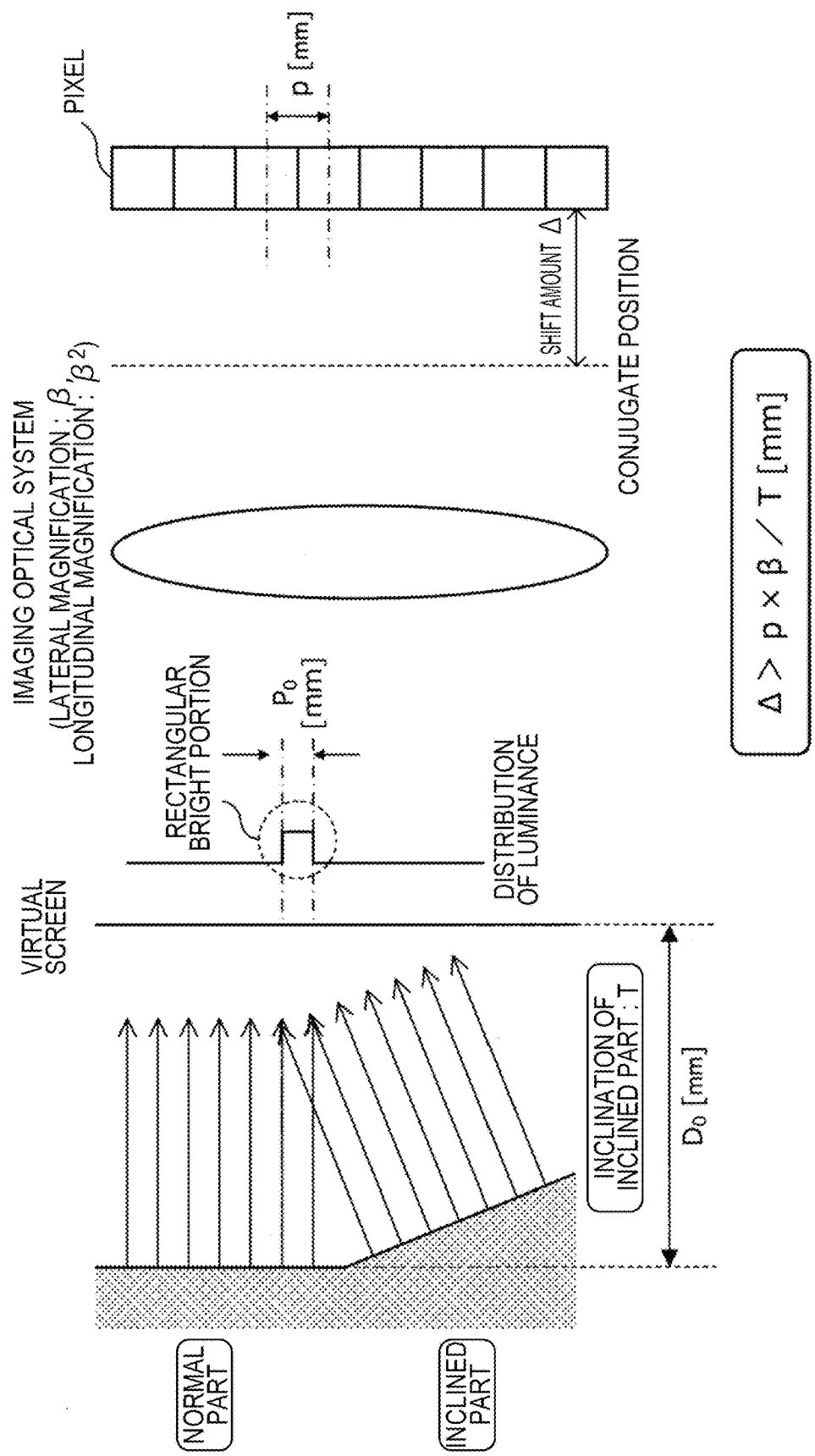
FIG. 11 is an explanatory diagram for describing an example of a method for deciding the shift amount from a conjugate position.
Figure 12:
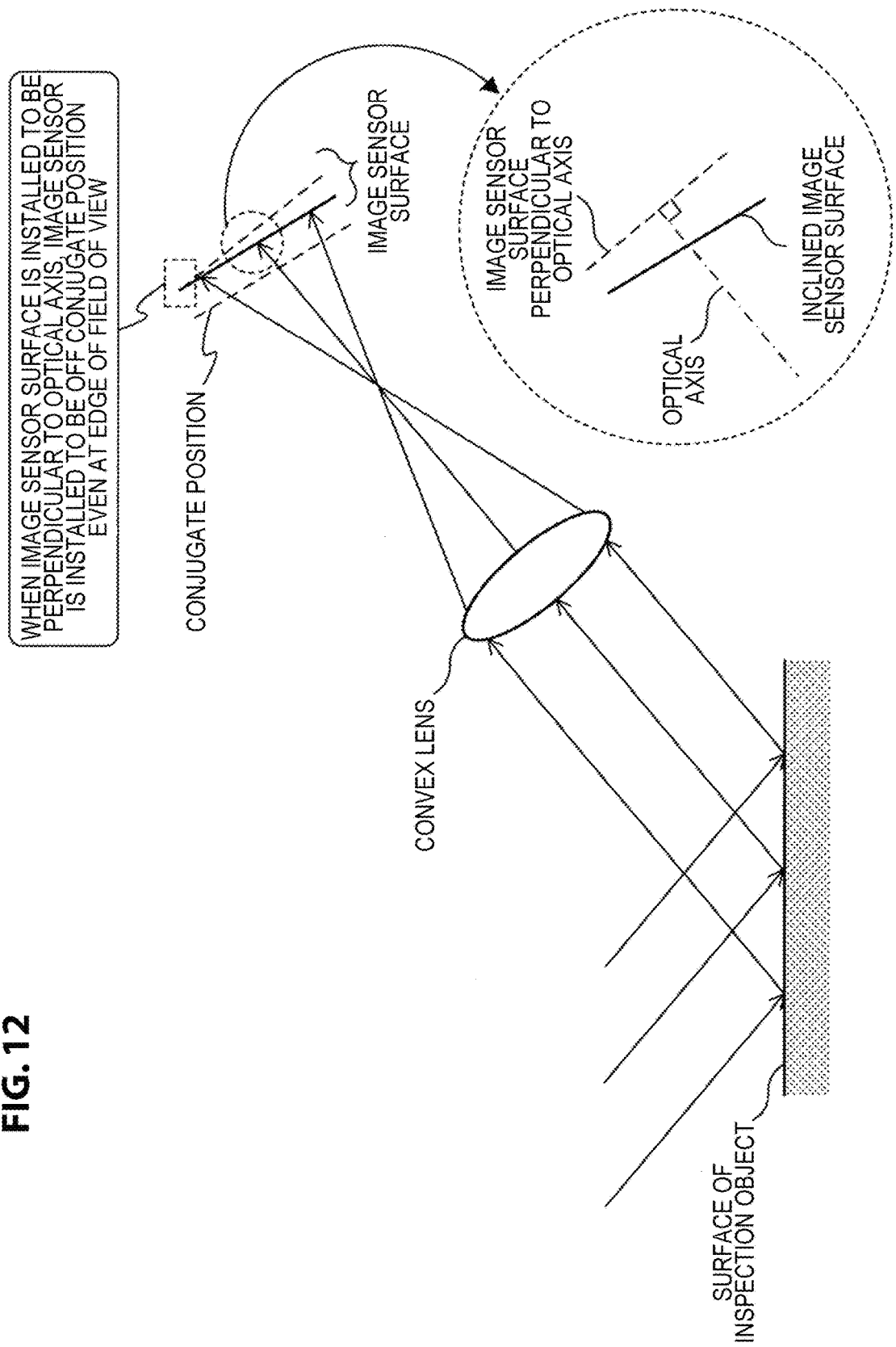
FIG. 12 is an explanatory diagram for describing an imaging unit of an inspection object imaging apparatus according to the embodiment.

FIG. 2 is an explanatory diagram schematically illustrating the overall configuration of the inspection object imaging apparatus 100 according to the present embodiment. FIGS. 3 to 5C are explanatory diagrams for describing a light source of an inspection object imaging apparatus according to the present embodiment. FIG. 6 is an explanatory diagram for describing a light source of an inspection object imaging apparatus according to the present embodiment. FIGS. 7 and 8 are explanatory diagrams illustrating examples of an imaging unit of an inspection object imaging apparatus according to an embodiment. FIG. 9 is an explanatory diagram for describing how an image is formed at a conjugate position. FIG. 10 is an explanatory diagram for describing an imaging unit of an inspection object imaging apparatus according to the present embodiment. FIG. 11 is an explanatory diagram for describing an example of a method for deciding the shift amount from a conjugate position. FIG. 12 is an explanatory diagram for describing an imaging unit of an inspection object imaging apparatus according to the present embodiment. FIG. 13 is an explanatory diagram for describing a light beam projecting unit of an inspection object imaging apparatus according to the present embodiment.

The inspection object imaging apparatus 100 according to the present embodiment includes a light beam projecting unit 101 and an imaging unit 103, as illustrated in FIG. 2.

[Light Beam Projecting Unit]

The light beam projecting unit 101 is an optical system for projecting a light beam of the infrared wavelength band on the surface of the inspection object S at a predetermined projection angle θ. This light beam projecting unit 101 includes, as illustrated in FIG. 2, a light source 105 that emits a light beam belonging to the infrared wavelength band (hereinafter also simply referred to as "infrared light"), and a projection optical system 107 that guides infrared light emitted from the light source 105 to the inspection object S. Here, the projection angle θ means an angle formed by the optical axis of the light source 105 and the direction normal to the surface of the inspection object S, as schematically illustrated in FIG. 2.

Figure 3:
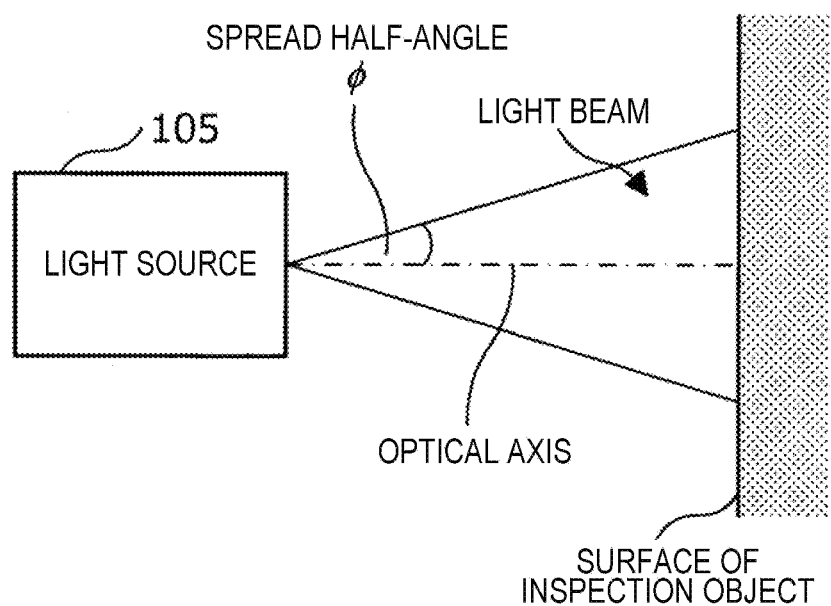
FIG. 3 is an explanatory diagram for describing a light source of an inspection object imaging apparatus according to the embodiment.

The light source 105 is configured to emit infrared light (e.g., infrared light of a wavelength of approximately 8 to 12 μm) to be applied to the surface of the inspection object S. This light source is a light source that emits a light beam of infrared light having a spread half-angle of a predetermined value or less. Here, the spread half-angle φ of a light beam means an angle that is formed by the optical axis of the light source 105 and a straight line indicating an outer edge of a light beam belonging to the infrared wavelength band that is emitted from the light source 105, as schematically illustrated in FIG. 3.

As will be described in detail later, in the inspection object imaging apparatus 100 according to the present embodiment, inclination present on the surface of an inspection object is visualized as light and dark of luminance values in a captured image. In addition, the surface inspection apparatus 10 according to the present embodiment detects inclination present on the surface of the inspection object on the basis of light and dark of luminance values in the captured image. Therefore, it is important that the light source 105 according to the present embodiment be a light source that enables precise reflection of inclination present on the surface of an inspection object.

Here, attention is focused on a case where the spread half-angle of a light beam emitted from the light source 105 is sufficiently smaller than inclination present on the surface of an inspection object.

Figure 4A:
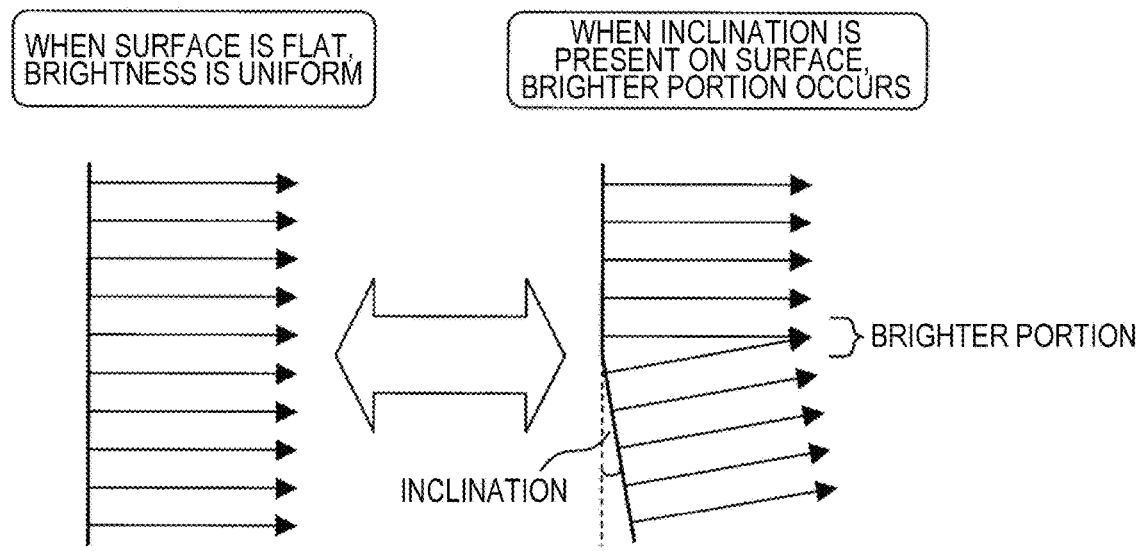
FIG. 4A is an explanatory diagram for describing a light source of an inspection object imaging apparatus according to the embodiment.

As schematically illustrated in the left drawing of FIG. 4A, in the case where the surface of the inspection object is flat, the brightness of light beams reflected at the surface is uniform because the light beams are reflected at the same reflection angle. As schematically illustrated in the right drawing of FIG. 4A, in the case where inclination is present on the surface of the inspection object, the reflection angle differs between a flat portion and an inclined portion; consequently, light beams of reflected light overlap each other to cause a brighter portion.

Now, attention is focused on a case where the spread half-angle of a light beam emitted from the light source 105 is larger than inclination present on the surface of an inspection object.

Figure 4B:
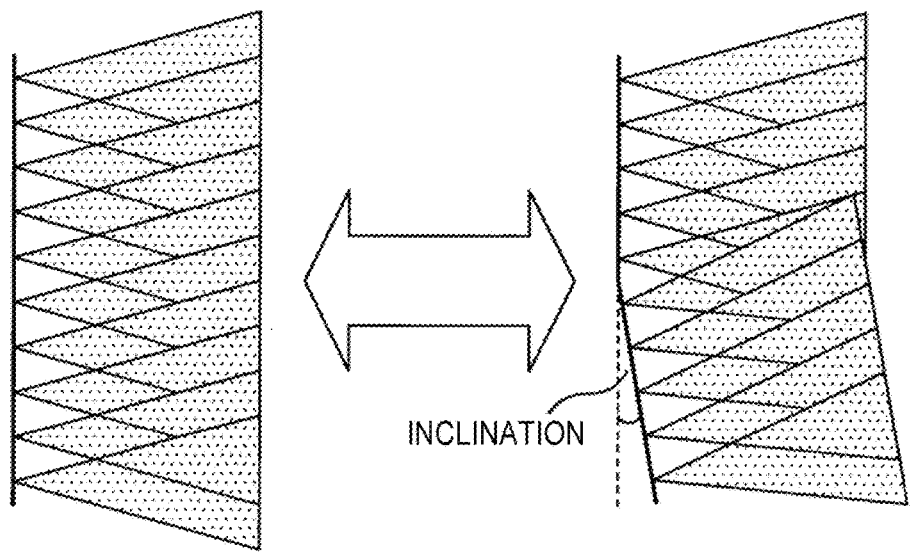
FIG. 4B is an explanatory diagram for describing a light source of an inspection object imaging apparatus according to the embodiment.

As schematically illustrated in the left drawing of FIG. 4B, light beams overlap each other even in the case where the surface of the inspection object is flat. Therefore, as schematically illustrated in the right drawing of FIG. 4B, when inclination is present on the surface of the inspection object, the change in brightness is small because light beams overlap each other also when the surface is flat; thus, it is difficult to detect inclination precisely.

On the basis of the findings described above, a light source that emits a light beam, a spread half-angle φ of the light beam on the surface of an inspection object being 20 times or less the minimum inclination of a surface to be imaged (in other words, the detection resolution of an inclination to be found), is used as the light source 105 according to the present embodiment. Here, it is not preferable that the spread half-angle φ of a light beam exceed 20 times the minimum inclination of a surface to be imaged, because it would be difficult to reflect inclination present on the surface of an inspection object. Note that the spread half-angle φ of a light beam is preferably as small as possible, and may be 0 degrees. The spread half-angle φ being 0 degrees means that a light beam emitted from the light source is complete parallel light.

Figure 5A:
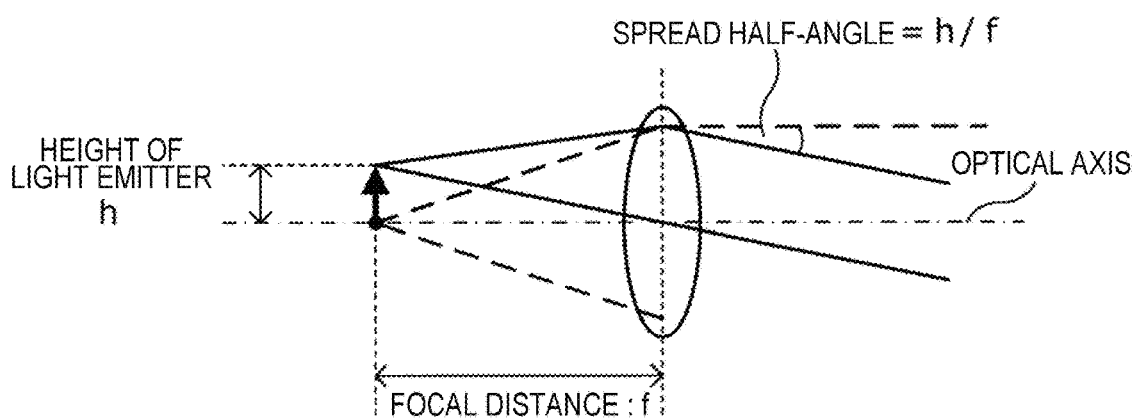
FIG. 5A is an explanatory diagram for describing a light source of an inspection object imaging apparatus according to the embodiment.
Figure 5B:
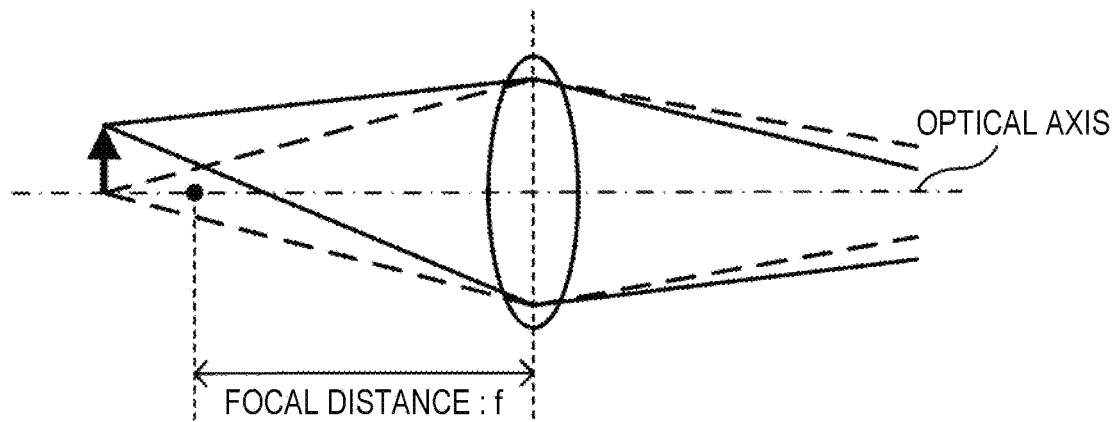
FIG. 5B is an explanatory diagram for describing a light source of an inspection object imaging apparatus according to the embodiment.
Figure 5C:
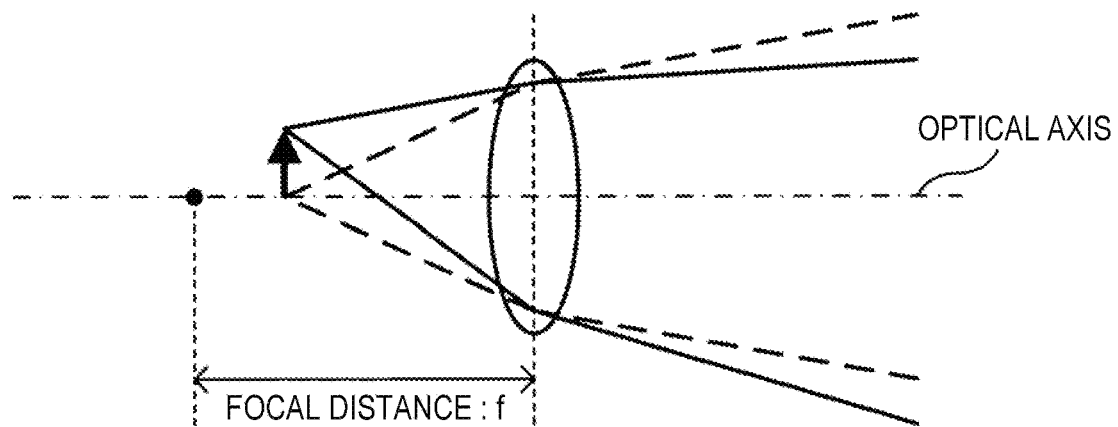
FIG. 5C is an explanatory diagram for describing a light source of an inspection object imaging apparatus according to the embodiment.

The light source 105 can be made to have such a spread half-angle by, for example, combining a convex lens with an infrared light emitter (hereinafter simply referred to as "light emitter") that radiates light in all directions from the surface, such as a red-hot object, as schematically illustrated in FIGS. 5A to 5C.

First, attention is focused on a case where the light emitter is positioned at the focus of the convex lens, as illustrated in FIG. 5A. In this case, an infrared light beam emitted from the light emitter passes through the convex lens to become parallel light. Here, the spread half-angle is a value expressed by h/f (unit: rad), where h is the height of the light emitter, which corresponds to a value of half the size of the light emitter, and f is the focal distance of the convex lens. Accordingly, if the focal distance f of the convex lens is constant, the spread half-angle becomes smaller as the height h of the light source becomes smaller (in other words, as the light emitter becomes closer to a point light source).

Next, attention is focused on a case where the light emitter is provided to be positioned on the rear side with respect to the focus of the convex lens (in other words, in a manner that the separation distance between the light emitter and the principal plane of the convex lens is larger than the focal distance f), as illustrated in FIG. 5B. In this case, an infrared light beam emitted from the light emitter passes through the convex lens to become convergent light.

In addition, attention is focused on a case where the light emitter is provided to be positioned on the front side with respect to the focus of the convex lens (in other words, in a manner that the separation distance between the light emitter and the principal plane of the convex lens is smaller than the focal distance f), as illustrated in FIG. 5C. In this case, an infrared light beam emitted from the light emitter passes through the convex lens to become divergent light.

Also in the cases illustrated in FIGS. 5B and 5C, the spread half-angle is expressed using the height h of the light emitter and the separation distance between an emission surface and the principal axis of the convex lens, and in the case where the separation distance is the same, the spread half-angle becomes smaller as the height h of the light source becomes smaller.

Thus, controlling the positional relationship between the light emitter and the convex lens makes it possible to select parallel light, convergent light, or divergent light as a light beam. In the inspection object imaging apparatus 100 according to the present embodiment, any of parallel light illustrated in FIG. 5A, convergent light illustrated in FIG. 5B, and divergent light illustrated in FIG. 5C can be used as a light beam emitted from the light source 105. Here, using parallel light as a light beam emitted from the light source 105 facilitates designing of optical systems of the inspection object imaging apparatus 100, because it eliminates constraints on the position where the whole light source 105 is provided. Accordingly, it is preferable to use parallel light illustrated in FIG. 5A as a light beam emitted from the light source 105.

The convex lenses illustrated in FIGS. 5A to 5C can double as the projection optical system 107 described later. Alternatively, the convex lenses illustrated in FIGS. 5A to 5C may be independent of the projection optical system 107 described later.

Instead of the combination of the light emitter and the convex lens described above, a combination of a laser element, such as a $CO_2$ laser, and an optical system can be used as the light source 105. In this case, a beam parameter product (BPP), which is the product of a beam radius and a spread half-angle of light emitted from the laser, is a constant peculiar to the element, and is an invariant during beam propagation; hence, the spread half-angle can be found by dividing the BPP by the radius of a light beam emitted from the light source 105, instead of using the height h of the light emitter as described above.

In the case of using a combination of a laser element and an optical system as the light source 105, in the present embodiment, it is preferable to use a quantum cascade laser (more specifically, a quantum cascade laser without an external resonator) as the light source 105. A quantum cascade laser without an external resonator is a laser light source capable of emitting infrared light having a wavelength of approximately 10 μm and a spectral bandwidth of approximately 400 nm. Using the quantum cascade laser as the light source 105 makes it possible to more effectively suppress the occurrence of speckle noise on the surface of an inspection object, as compared with the case of using another infrared light source. Also in the case where a quantum cascade laser is used as the light source 105, the spread half-angle can be found by dividing a BPP, which is a constant peculiar to the element, by the radius of a light beam emitted from the light source 105.

FIG. 6 shows a captured image obtained by imaging a convexity present on the surface of a steel sheet, by using a $CO_2$ laser light source or a quantum cascade laser light source without an external resonator as the light source 105. Here, the $CO_2$ laser light source used is a light source that emits a light beam having a center wavelength of 10.6 μm and a spectral bandwidth of 1 nm, and the quantum cascade laser light source used is a light source that emits a light beam having a center wavelength of 10 μm and a spectral bandwidth of 400 nm. Note that in acquiring the captured images shown in FIG. 6, a light beam emitted from each light source is made into parallel light and then applied to the surface of the steel sheet. It is apparent from comparison between the two captured images shown in FIG. 6 that in the case where a $CO_2$ laser is used as the light source 105, speckle noise has occurred in the entire captured image, and the convexity (a portion that appears black) present near the center of the image is unclear. In the case where a quantum cascade laser is used as the light source 105, occurrence of speckle noise is suppressed, and the convexity (a portion that appears black) present near the center of the image is shown clearly.

Here, the light source 105 may be a continuous wave (CW) laser light source capable of emitting CW light, or may be a pulsed laser light source capable of emitting pulsed light. Here, in the case where the inspection object S is moving on a production line, for example, the moving inspection object S can be imaged in a still state even when a CW laser light source is used as the light source 105, in the case where the amount of movement of the inspection object S within one frame time of an image sensor in an infrared camera provided in the imaging unit 103 described later is ignorable. In the case where a pulsed laser light source is used as the light source 105, the moving inspection object S can be imaged in a still state.

For convenience, a case where parallel infrared light is emitted from the light source 105 is described below as an example. Note that an effect similar to that with parallel infrared light can be enjoyed also in the case where convergent infrared light or divergent infrared light is emitted from the light source 105.

The projection optical system 107 guides infrared light emitted from the light source 105 in a manner that the infrared light is projected on the surface of the inspection object S at a predetermined projection angle θ. The projection optical system 107 is preferably configured to change only the direction of a light beam, without changing the size of a light beam, so that the spread half-angle of a light beam emitted from the light source 105 does not change.

In the light beam projecting unit 101 according to the present embodiment, various reflecting mirrors for changing the propagation direction of infrared light may be provided as the projection optical system 107.

The material of the projection optical system 107 according to the present embodiment may be selected as appropriate in accordance with the wavelength of infrared light that is used, from among materials applicable to infrared light, such as germanium (Ge) and zinc selenide (ZnSe).

The light beam projecting unit 101 according to the present embodiment, in which the installation position and the installation direction of the light source 105 are adjusted, and reflecting mirrors and the like installed as the projection optical system 107 are combined as appropriate, projects infrared light having a predetermined spread half-angle on the surface of the inspection object S at the projection angle θ.

Here, the projection angle θ of infrared light emitted from the light beam projecting unit 101 is set in a manner that the surface of the inspection object S can be regarded as a specular surface. A method for setting the projection angle θ of infrared light is briefly described below.

In the inspection object imaging apparatus 100 according to the present embodiment, a formula of a specularity parameter g (Formula 101) described in Non-Patent Literature 1 is used in deciding the projection angle θ. The specularity parameter g expressed by Formula 101 below indicates the degree of specularity of an object surface, and when the value of the parameter g is small, the object surface of interest can be considered to be a specular surface. In Formula 101 below, a parameter σ is standard deviation of the amount of unevenness (i.e., surface roughness) of the object surface of interest, and a parameter λ is the wavelength of light that is used. A parameter $\theta_1$ is the angle of incidence of light to the object surface of interest, and a parameter $\theta_2$ is the angle of emission of light from the object surface of interest. On the assumption that the angle of incidence and the angle of emission are θ, Formula 101 below can be transformed into Formula 101a.

[Math. 3]

$$g = \left\{ \frac{2\pi\sigma}{\lambda} \cdot (\cos\theta_1 + \cos\theta_2) \right\}$$ (Formula 101)

$$g = \left\{ \frac{4\pi\sigma}{\lambda} \cdot \cos\theta \right\}$$ (Formula 101a)

Here, in the present embodiment, the parameter λ, in Formula 101 and Formula 101a above is a value determined in accordance with an infrared light source used as the light source 105. The parameter σ is a value that can be decided on the basis of findings obtained from operation data or the like related to a production track record of the inspection object S of interest.

If the value of the specularity parameter g expressed by Formula 101 or Formula 101a is 1 or more, a diffuse reflection component increases and a specular reflection component rapidly decreases on the object surface of interest. Accordingly, in the inspection object imaging apparatus 100 according to the present embodiment, the angle θ (i.e., the projection angle θ of infrared light) is decided in a manner that the value of the specularity parameter g expressed by Formula 101 or Formula 101a is 1 or less, in accordance with the values of the parameter λ and the parameter σ decided as design parameters.

For example, in the case where the parameter λ (wavelength) is 10.6 μm, and the parameter σ is 1 μm, the specularity parameter g can be 1 or less when the angle θ is set to 32 degrees or more.

[Imaging Unit]

Now, the imaging unit 103 included in the inspection object imaging apparatus 100 according to the present embodiment will be described in detail.

The imaging unit 103 according to the present embodiment includes an imaging optical system 109 and two infrared cameras 111 and 113, as illustrated in FIG. 2.

The imaging optical system 109 is configured to guide reflected light of parallel infrared light from the surface of an inspection object to image sensors of the infrared cameras 111 and 113 described later. As the imaging optical system 109, a condensing optical element for condensing reflected light from the surface of the inspection object S, a branching optical element for branching reflected light that has passed through the condensing optical element to the infrared cameras 111 and 113 described later, and the like are provided.

Here, the condensing optical element is configured to condense reflected light from the surface of the inspection object S, as described above, to form images in the infrared cameras 111 and 113, and includes at least one convex lens. The imaging unit 103 according to the present embodiment may include, as the condensing optical element of the imaging optical system 109, only one convex lens, a lens group in which a plurality of convex lenses are combined, or a lens group in which a convex lens is combined with various concave lenses, an aspherical lens, etc.

In the imaging unit 103 according to the present embodiment, including at least one convex lens as the condensing optical element reduces constraints on routing of an optical path, which results in an improvement in design flexibility of an optical system. Thus, the inspection object imaging apparatus 100 according to the present embodiment enables a reduction in size of an apparatus and a reduction in installation space.

The branching optical element is configured to branch reflected light that has passed through the condensing optical element into two optical paths, as described above, and may be a beam splitter, for example. Reflected light is branched by the branching optical element to be guided to the image sensor of the infrared camera 111 and the image sensor of the infrared camera 113.

In addition, the imaging unit 103 according to the present embodiment may include a condensing optical element, which is an example of a condensing optical system, for condensing reflected light that has passed through the branching optical element onto the image sensor, between the branching optical element and the image sensor of each infrared camera. The condensing optical element may be installed in the imaging unit 103 as a type of the imaging optical system 109, or may be installed in the imaging unit 103 as a lens of the infrared camera described later. Providing the condensing optical element enables an improvement in design flexibility of the imaging unit 103 as will be described later.

In the imaging unit 103 according to the present embodiment, various reflecting mirrors for changing the propagation direction of reflected light may be provided as the imaging optical system 109.

The material of the imaging optical system 109 according to the present embodiment may be selected as appropriate in accordance with the wavelength of infrared light that is used, from among materials applicable to infrared light, such as germanium (Ge) and zinc selenide (ZnSe).

The infrared cameras 111 and 113 each image infrared light (e.g., parallel infrared light) reflected at the surface of the inspection object S with an image sensor provided in the camera, to generate a captured image of reflected light. As the image sensor provided in each of the infrared cameras 111 and 113, for example, a semiconductor array of HgCdTe, InSb, or the like, or a thermal sensor array, such as a microbolometer, can be used, as long as it supports imaging of infrared light. In addition to these sensors, any image sensor suitable for imaging infrared light can be used.

Here, the image sensors of the infrared cameras 111 and 113 included in the imaging unit 103 according to the present embodiment are each installed in a place on the optical path that is shifted from a position conjugate with the surface of the inspection object S, as will be described later. Here, conjugate refers to a state where light that has diverged from one point on the surface of the inspection object S is caused to converge on one point on an image by the imaging optical system 109 (i.e., the relationship between an object and an image in an image formation state), and it is apparent that in the case where the object and the image are replaced with each other, the image formation relationship holds similarly when a ray is traced reversely. That is, in the present embodiment, light emitted from one point on the inspection object S enters different positions on an image sensor surface of each infrared camera, depending on its direction. In other words, in the present embodiment, the image sensor of each of the infrared cameras 111 and 113 is installed to make a state not satisfying an image formation relationship.

Here, a configuration of the imaging unit 103 according to the present embodiment is described in detail with specific examples, with reference to FIGS. 7 and 8.

Specific Example 1 of Imaging Unit

First, an example of an imaging unit is specifically described with reference to FIG. 7.

In the example illustrated in FIG. 7, as the imaging optical system 109 included in the imaging unit 103, a convex lens 121, which is an example of a condensing optical element, is provided, and a beam splitter BS that branches reflected light that has passed through the convex lens 121 into two optical paths is provided as a branching optical element on the optical axis of reflected light. Reflected light branched into two by the beam splitter BS form images on a sensor surface of an image sensor 123 of the infrared camera 111 and a sensor surface of an image sensor 125 of the infrared camera 113.

Here, the separation distance L1 between the surface of an inspection object and the convex lens 121 in FIG. 7 may be set as appropriate in accordance with work distance or the like in the actual inspection site. The focal distance f1 of the convex lens 121 is a value determined in accordance with the type of a convex lens that is used. In this case, the image formation formula of the imaging unit 103 illustrated in FIG. 7 is expressed by Formula 111 below, where L2 is the separation distance between the convex lens 121 and the image sensor of each infrared camera.

[Math. 4]

$$\frac{1}{f1} = \frac{1}{L1} + \frac{1}{L2} \qquad \text{(Formula 111)}$$

Here, a position of the separation distance L2 that satisfies Formula 111 above corresponds to a position conjugate with the surface of the inspection object (hereinafter also simply referred to as a conjugate position). Hence, in the example of the imaging unit 103 illustrated in FIG. 7, the sensor surface of the image sensor 123 of the infrared camera 111 is installed to be shifted from the conjugate position so that the separation distance from the convex lens 121 on the optical axis is (L2+Δ). Similarly, the sensor surface of the image sensor 125 of the infrared camera 113 is installed to be shifted from the conjugate position so that the separation distance from the convex lens 121 on the optical axis is (L2−Δ).

Specific Example 2 of Imaging Unit

Now, another example of an imaging unit is specifically described with reference to FIG. 8.

In the imaging unit illustrated in FIG. 7, when the separation distance L1 between the surface of an inspection object and the convex lens and the focal distance f1 of the convex lens are decided, the separation distance L2 between the convex lens and the image sensor is determined, and consequently imaging magnification (L1/L2) is also determined. Therefore, it can be said that the example of the imaging unit illustrated in FIG. 7 has low design flexibility of an optical system.

Hence, in the example of the imaging unit illustrated in FIG. 8, lenses 127 and 129 are installed respectively as condensing optical elements between the convex lens 121, which is an example of a condensing optical element, and the image sensors 123 and 125 (more specifically, between the beam splitter BS, which is an example of a branching optical element, and the image sensors 123 and 125). This enables an improvement in design flexibility of an optical system in the imaging unit illustrated in FIG. 8, as described below.

First, in the optical system illustrated in FIG. 8, work distance is set in accordance with the focal distance f1 of the convex lens 121 that is used, and the separation distance between the surface of an inspection object and the convex lens is set to the focal distance f1. After that, in accordance with the size D of the field of view of the inspection object and the size d of an image sensor that is used, the focal distance f2 of the lenses 127 and 129 installed as condensing optical elements is decided on the basis of Formula 121 below. On this occasion, the imaging magnification of the imaging optical system is a value expressed by (f2/f1).

[Math. 5]

$$\frac{f2}{f1} = \frac{d}{D}$$ (Formula 121)

On this occasion, if the separation distances between the lenses 127 and 129 serving as condensing optical elements and sensor surfaces of the image sensors are set equal to the focal distance f2, the installation positions of the sensor surfaces are positions conjugate with the surface of the inspection object. Hence, in the example of the imaging unit 103 illustrated in FIG. 8, the sensor surface of the image sensor 123 of the infrared camera 111 is installed to be shifted from the conjugate position so that the separation distance from the lens 127 on the optical axis is (f2+Δ). Similarly, the sensor surface of the image sensor 125 of the infrared camera 113 is installed to be shifted from the conjugate position so that the separation distance from the lens 129 on the optical axis is (f2−Δ).

Here, as illustrated in FIG. 8, the separation distance between the convex lens 121, which is an example of a condensing optical element, and each of the lenses 127 and 129 is set to (f1+f2); thus, the imaging unit 103 can serve as a telecentric optical system. In the case where the imaging unit 103 is a telecentric optical system, even when the shift amount Δ from the conjugate position differs between the infrared camera 111 and the infrared camera 113, images formed in the image sensors of the cameras can have the same size.

However, in the imaging unit 103 according to the present embodiment, it is not essential for the optical system to be a telecentric optical system, as long as the surface of the inspection object and the sensor surface of the image sensor are in an arrangement with the shift amount Δ from a conjugate arrangement. Note that in the case where the imaging unit 103 is not a telecentric optical system, the infrared camera 111 and the infrared camera 113 capture images of different sizes.

The imaging unit 103 according to the present embodiment has been specifically described with reference to FIGS. 7 and 8.

In the specific examples illustrated in FIGS. 7 and 8, cases where each of the lenses 121, 127, and 129 is one convex lens are illustrated, but the number of optical elements according to the present embodiment is not limited to that in the drawing, and each lens in the drawing may be a lens group composed of a plurality of lenses.

Installation Position of Image Sensor

Next, description is given on a reason for installing an image sensor mounted on an infrared camera in a place that is shifted from a position conjugate with the surface of an inspection object, with reference to FIGS. 9 and 10.

Assume that unevenness is present on the surface of an inspection object, as illustrated in FIG. 9. In this case, infrared light (e.g., parallel infrared light) applied to the unevenness portion is changed in direction by the unevenness, and propagates in a travel direction (a direction indicated by the dotted line in the drawing) that is different from a travel direction of light when no unevenness is present (a direction indicated by the solid line in the drawing). Consequently, infrared light reflected at the unevenness portion on the surface of the inspection object enters a convex lens from a position that is different from the position of light entering the convex lens when no unevenness is present. As a result, infrared light reflected at the unevenness portion propagates in a direction that is different from the propagation direction of reflected light when no unevenness is present.

However, it is apparent from the technical meaning of the term "conjugate" that, at a position conjugate with the surface of the inspection object, infrared light reflected at the same point forms an image at the same position even in the case where unevenness is present on the surface of the inspection object, as illustrated in the drawing. Accordingly, at the position conjugate with the surface of the inspection object, a change in density of light beams (i.e., a change in brightness) does not occur; thus, the state of unevenness cannot be visualized.

FIG. 10 is an enlarged view schematically illustrating the state of a light beam around a conjugate position. In FIG. 10, arrows correspond to reflected light from individual points on the surface of an inspection object (i.e., an inspection target surface). In the case where no unevenness is present on the inspection target surface, infrared light (e.g., parallel infrared light) reflected at each point propagates without a change in direction of light; thus, sparseness and denseness do not occur in the density of light beams, regardless of whether or not the position is a conjugate position.

On the other hand, in the case where unevenness is present on the surface, at the conjugate position, a point at which light forms an image coincides with an image formation point when no unevenness is present; thus, no change occurs in the density of light beams. However, in a place closer to the object than the conjugate position by Δ and a place closer to the image than the conjugate position by Δ, a difference in propagation direction of light causes a change in the density of light beams, causing a portion with sparse light beams and a portion with dense light beams. Consequently, in places other than the conjugate position, a place that is darker than the surroundings (a portion with sparse light beams) occurs, and a place that is brighter than the surroundings (a portion with dense light beams) occurs.

In the imaging unit 103 according to the present embodiment, one of two image sensors provided in two infrared cameras is placed on the front side (object side) with respect to the conjugate position, and the other is placed further ahead (on the image side) with respect to the conjugate position. Consequently, owing to the phenomenon described above, a spot corresponding to an unevenness portion appears darker than the surroundings in a captured image obtained in one image sensor, and a spot corresponding to an unevenness portion appears brighter than the surroundings in a captured image obtained in the other image sensor.

Whether the object side with respect to the conjugate position is dark or bright changes depending on whether a convexity is present or a concavity is present on the inspection target surface. Accordingly, by performing verification beforehand using samples whose unevenness states are known, it is possible to find a combination of light and dark when a concavity is present and a combination of light and dark when a convexity is present. In the arithmetic processing apparatus 200 described later, unevenness present on the surface of an inspection object can be detected by using this finding.

On the other hand, in the case where dirt is present on the inspection target surface, inversion of light and dark between the front and rear with respect to the conjugate position, which is described above, does not occur. Accordingly, in the case where captured images obtained from the image sensors are compared and there is no inversion of light and dark, it can be determined that unevenness is not present in the corresponding portion, but a portion with different reflectance has been caused by presence or absence of dirt or a difference in roughness.

Now, description will be given on an example of a method for deciding a shift amount Δ from a conjugate position, with reference to FIG. 11.

As illustrated in FIG. 11, assume a sample in which a normal part without unevenness and an inclined part whose surface is inclined by unevenness are adjacent to each other. If a virtual screen that receives reflected light is installed in the vicinity of the surface, overlapping of light beams causes a rectangular bright portion to appear on the virtual screen. The size of the bright portion on a sensor when observed with a camera focused on the rectangular bright portion may be one pixel or more. To focus the camera, it is necessary to move the sensor, and the amount of this movement is equal to the minimum value of a necessary shift amount Δ.

As illustrated in FIG. 11, assume that the virtual screen is present at a position apart from the sample by $D_o$ [mm], and the size of the rectangular bright portion shown on the virtual screen is $P_o$ [mm]. In this case, the bright portion appears as an image with a size of $P_o \times \beta$ [mm] on the sensor, where β is the lateral magnification of the imaging optical system 109. Accordingly, to detect the bright portion in a size larger than one pixel on the sensor, it is necessary to satisfy a condition expressed by Formula 131 below, where p [mm] is the size of one pixel (a pixel pitch).

[Math. 6]

$$P_o \times \beta > p \quad \text{(Formula 131)}$$

Here, the amount of movement of the conjugate position on the image side when the sample is moved $D_o$ [mm] in the optical axis direction on the object side is expressed by longitudinal magnification, and the amount of movement is the square of the lateral magnification β ($\beta^2$). Accordingly, the shift amount Δ [mm] from the conjugate position that is needed to bring the virtual screen into focus is a value expressed by Formula 132 below.

[Math. 7]

$$\Delta = D_o \times \beta^2 \quad \text{(Formula 132)}$$

When the inclination of the inclined part is denoted by T, its magnitude can be expressed by Formula 133 below, by using the separation distance $D_o$ between the virtual screen and the sample and the size $P_o$ of the rectangular bright portion.

[Math. 8]

$$T = \frac{P_o}{D_o} \quad \text{(Formula 133)}$$

Accordingly, when $P_o$ and $D_o$ are erased from Formulas 131 to 133 above, the minimum value of the shift amount Δ is given as shown in Formula 134 below.

[Math. 9]

$$\Delta > \frac{p \cdot \beta}{T} \quad \text{(Formula 134)}$$

As shown in Formula 134 above, the minimum value of the shift amount Δ from the conjugate position can be calculated on the basis of the inclination of a flaw (unevenness flaw) to be imaged (in other words, to be detected), the pixel size (pixel pitch) of an image sensor, and the lateral magnification of an imaging optical system. Here, the lateral magnification β of the optical system is a value that can be calculated from design parameters of the imaging unit 103. In addition, the inclination of a flaw to be imaged (a flaw to be detected) can be decided by using findings that are obtained from track record data in the past related to production of a metal plate to be inspected.

For example, assume that, in the imaging unit 103 illustrated in FIG. 8, the focal distance f1 is 500 mm, and the focal distance f2 is 35 mm. In this case, the lateral magnification of the imaging unit 103 is 35/500=0.07 according to (f2/f1). On the assumption that the pixel pitch p of the image sensor is 38 μm, the shift amount Δ for imaging (detecting) a flaw with an inclination T of (1/1000) is $38 \times 10^{-3} \times 0.07 \times 1000 \approx 2.6$ mm, according to Formula 134 above.

The shift amount Δ from the conjugate position, which is set by using the values calculated in the above way, may be different or may be the same between the image sensor installed on the inspection object side with respect to the conjugate position and the image sensor installed further on the infrared-light travel direction side with respect to the conjugate position.

Method for Installing Image Sensor

Now, description will be given on a method for installing an image sensor in an imaging optical system according to the present embodiment, with reference to FIG. 12.

In general, an image sensor for imaging reflected light is often installed in a manner that its sensor surface (hereinafter also referred to as an image sensor surface) is perpendicular to the optical axis. On the other hand, as illustrated in FIG. 12, a plane conjugate with the surface of an inspection object is in a state of being inclined with respect to the optical axis. Accordingly, in the case where the image sensor surface is installed to be perpendicular to the optical axis, the image sensor is installed to be off the conjugate position even at an edge of the field of view of the image sensor, and focus is decided.

When infrared light (e.g., parallel infrared light) is caused to enter the surface of an inspection object obliquely as in the inspection object imaging apparatus 100 according to the present embodiment, in the case where the image sensor surface is perpendicular to the optical axis, the shift amount Δ from the conjugate position slightly differs between places on the image sensor surface, which causes a difference in appearance of reflected light. Hence, as illustrated in FIG. 12, the image sensor surface may be inclined with respect to the optical axis to prevent the shift amount Δ from the conjugate position from changing in the field of view. This makes the shift amount Δ from the conjugate position constant in the field of view; thus, light and dark on the image sensor exhibit uniform sensitivity to unevenness of an inspection object.

Moreover, even in the case where the image sensor surface is perpendicular to the optical axis, a so-called tilt lens may be installed on the front side (inspection object surface side) with respect to the image sensor for tilt photography. Installing the tilt lens on the front side with respect to the image sensor causes the image sensor surface to be optically inclined with respect to the optical axis, making the shift amount Δ from the conjugate position substantially constant in the field of view.

The imaging unit 103 according to the present embodiment has been described in detail with reference to FIGS. 3 to 12.

Method for Imaging Inspection Object Present in Curved State

On production lines, various metal plates are conveyed through a curved part, such as a roll winding part, or wound around a roll winding part in some cases. In the inspection object imaging apparatus 100 according to the present embodiment, the light beam projecting unit 101 and the imaging unit 103 can include an optical element described below to enable imaging of not only an inspection object such as a metal plate placed on a plane, but also an inspection object present in a curved state.

An example of a method for imaging an inspection object present in a curved state will be described with reference to FIG. 13. FIG. 13 is an explanatory diagram for describing an example of the projection optical system 107 and the imaging optical system 109 of an inspection object imaging apparatus according to the present embodiment.

To image an inspection object present in a curved state, a convex cylindrical lens illustrated in FIG. 13 that condenses parallel infrared light and guides it to the inspection object may be further provided as part of the projection optical system 107. As illustrated in the upper stage of FIG. 13, the focal distance and installation position of this convex cylindrical lens are designed in a manner that incident parallel light is condensed toward the rotation center axis of a roll, and, as viewed in the axial direction of a roll winding part, parallel infrared light enters a curved part in a direction parallel to the direction normal to the roll surface. As illustrated in the lower stage of FIG. 13, as viewed from above, parallel infrared light enters the inspection object present in a curved state in an oblique direction. The angle of incidence in the oblique direction as viewed from above is decided in a manner that the parameter g shown in Formula 101a above is 1 or less.

Light reflected at the surface of the inspection object is divergent light, but enters the convex cylindrical lens illustrated in FIG. 13, which also serves as part of the imaging optical system 109, to return to parallel light, and goes through the rest of the imaging optical system to be imaged by an infrared camera.

On this occasion, the focal distance of the convex cylindrical lens is preferably set in a manner that the focus of the lens is the rotation center axis of the roll, that is, to be a distance from the position of the roll rotation axis to the convex cylindrical lens.

Providing such a cylindrical lens in the projection optical system 107 and the imaging optical system 109 enables favorable imaging of reflected light, even for an inspection object present in a curved state.

A case where one cylindrical lens is used is described in FIG. 13, but a cylindrical lens of the projection optical system 107 and a cylindrical lens of the imaging optical system 109 may be separately installed with different installation positions and focal distances.

The inspection object imaging apparatus 100 according to the present embodiment has been described in detail with reference to FIGS. 3 to 13.

<Configuration of Arithmetic Processing Apparatus>

[Overall Configuration of Arithmetic Processing Apparatus]

Figure 14:
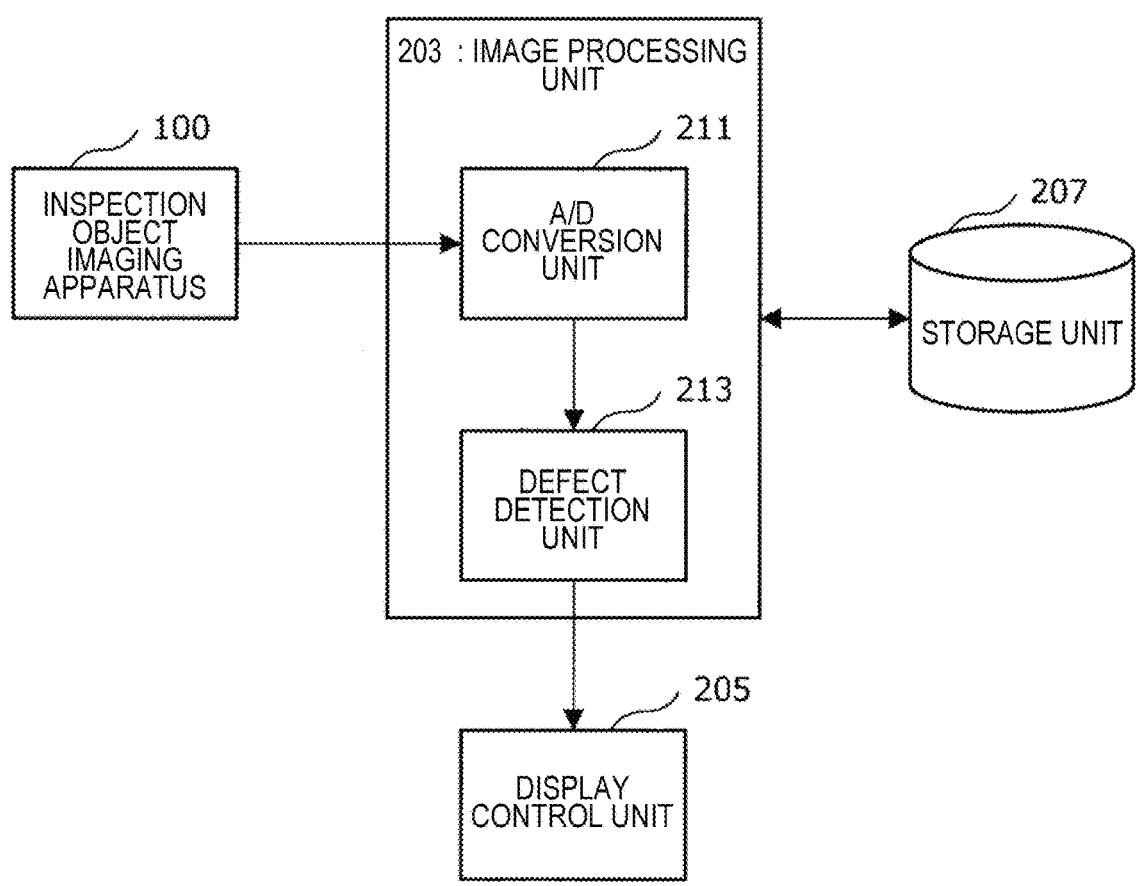
FIG. 14 is a block diagram illustrating a configuration of an image processing unit of an arithmetic processing apparatus according to the embodiment.

Now, a configuration of the arithmetic processing apparatus 200 according to the present embodiment will be described in detail with reference to FIGS. 1 and 14.

First, referring back to FIG. 1, brief description is given on an overall configuration of the arithmetic processing apparatus 200 according to the present embodiment.

As illustrated in FIG. 1, the arithmetic processing apparatus 200 according to the present embodiment mainly includes an imaging control unit 201, an image processing unit 203, a display control unit 205, and a storage unit 207.

The imaging control unit 201 is configured with a central processing unit (CPU), a read only memory (ROM), a random access memory (RAM), a communication device, and the like. The imaging control unit 201 controls imaging of an inspection target by the inspection object imaging apparatus 100 according to the present embodiment. Specifically, in starting the imaging of the inspection object S, the imaging control unit 201 sends a controls signal for starting emission of infrared light to the inspection object imaging apparatus 100.

When the inspection object imaging apparatus 100 starts to apply infrared light to the inspection object S, the imaging control unit 201 sends trigger signals for starting imaging of reflected light to the two infrared cameras 111 and 113 included in the inspection object imaging apparatus 100.

The image processing unit 203 is configured with, for example, a CPU, a ROM, a RAM, a communication device, and the like. The image processing unit 203 uses imaging data acquired from the inspection object imaging apparatus 100 (more specifically, the infrared cameras 111 and 113 of the inspection object imaging apparatus 100) to perform image processing, which will be described later, and performs a surface inspection process for detecting a defect (dirt or an unevenness flaw) that may be present on the surface of a metal plate, which is the inspection object S. Upon ending the surface inspection process for the surface of the inspection object S, the image processing unit 203 transmits information on the obtained inspection results to the display control unit 205.

This image processing unit 203 will be described in detail later.

The display control unit 205 is configured with, for example, a CPU, a ROM, a RAM, an output device, and the like. The display control unit 205 performs display control in displaying surface inspection results of the inspection object S to be inspected, which are transmitted from the image processing unit 203, on an output device (e.g., a display) included in the arithmetic processing apparatus 200, an output device provided outside the arithmetic processing apparatus 200, or the like. Thus, a user of the surface inspection apparatus 10 can recognize on-site inspection results related to various defects present on the surface of the inspection object S.

The storage unit 207 is an example of a storage device included in the arithmetic processing apparatus 200. In the storage unit 207, various parameters and process intermediate progresses that the arithmetic processing apparatus 200 according to the present embodiment needs to save when performing some sort of process, various databases and programs, or the like are recorded as appropriate. With regard to this storage unit 207, the imaging control unit 201, the image processing unit 203, the display control unit 205, and the like can perform reading/writing freely.

[Configuration of Image Processing Unit]

Now, a configuration of the image processing unit 203 included in the arithmetic processing apparatus 200 according to the present embodiment will be described with reference to FIG. 14. FIG. 14 is a block diagram illustrating a configuration of an image processing unit included in the arithmetic processing apparatus 200 according to the present embodiment.

As illustrated in FIG. 11, the image processing unit 203 according to the present embodiment further includes an A/D conversion unit 211 and a defect detection unit 213.

The A/D conversion unit 211 is configured with, for example, a CPU, a ROM, a RAM, and the like. The A/D conversion unit 211 A/D-converts captured images output from the infrared cameras 111 and 113 of the inspection object imaging apparatus 100 into digital multi-valued image data. After that, the A/D conversion unit 211 outputs the generated digital multi-valued image data to the defect detection unit 213 described later.

In addition, the A/D conversion unit 211 may contain the generated digital multi-valued image data in an image memory provided in the storage unit 207 or the like, in association with time information on date and time at which the data is generated.

The defect detection unit 213 is configured with, for example, a CPU, a ROM, a RAM, and the like. The defect detection unit 213 uses two types of digital multi-valued image data that correspond to images captured by the infrared cameras 111 and 113 of the inspection object imaging apparatus 100 to detect a defect area, such as dirt or an unevenness flaw, present on the surface of the inspection object S.

For pixels constituting the two types of digital multi-valued image data, the defect detection unit 213 specifies a pixel with a pixel value smaller than that of a surrounding pixel (i.e., a pixel that is darker than the surroundings) and a pixel with a pixel value larger than that of a surrounding pixel (i.e., a pixel that is brighter than the surroundings). Such a spot corresponds to a spot where dirt or an unevenness flaw has occurred. Moreover, the defect detection unit 213 connects consecutive defect spots, thereby specifying each defect area.

Then, the defect detection unit 213 compares the captured images obtained from the infrared cameras 111 and 113, and determines how light and dark are combined for corresponding defect areas. In the case where defect areas specified from the infrared cameras 111 and 113 have a combination of light-light or a combination of dark-dark, the defect detection unit 213 determines that the area is an area with different reflectance that is caused by dirt or the like. In addition, the defect detection unit 213 determines that an area exhibiting a combination of light-dark or a combination of dark-light is an area where an unevenness flaw has occurred. The defect detection unit 213 further specifies whether the area exhibiting a combination of light-dark or a combination of dark-light is a convexity or a concavity.

Upon specifying a defect area present on the surface of the inspection object S in the above way, the defect detection unit 213 outputs information on the specified defect area to the display control unit 205.

Moreover, the defect detection unit 213 according to the present embodiment may have, in addition to a defect area specifying function of specifying a defect area as described above, a feature value extracting function of extracting feature values related to the form and pixel values of the specified defect area, and a defect identifying function of identifying the category, degree of harmfulness, etc. of a defect on the basis of the extracted feature values. These functions are briefly described below.

Feature Value Extracting Function

Upon specifying defect areas (unevenness areas) in captured images by the defect area specifying function, the defect detection unit 213 extracts feature values related to the form and pixel value of the defect area for each of the specified defect areas. Examples of a feature value related to the form of a defect area include the width of the defect area, the length of the defect area, the perimeter of the defect area, the area of the defect area, and the area of a circumscribed rectangle of the defect area. Examples of a feature value related to the pixel values of a defect area include the maximum value, the minimum value, and the average value of luminance of the defect area.

Defect Identifying Function

Upon extracting feature values of the defect areas by the feature value extracting function, the defect detection unit 213 identifies the category, degree of harmfulness, etc. of a defect on the basis of the extracted feature values, for each of the defect areas. An identification process of the category, degree of harmfulness, etc. of a defect based on feature values is performed by using a logic table, for example.

Categories of defects are written as items in the vertical direction of the logic table, and types of feature values are written as items in the horizontal direction of the logic table. In addition, in each cell of the table that is defined by the category and feature value of a defect is written an identification condition formula based on the magnitude of the corresponding feature value. Each row of this logic table serves as a set of category identification conditions of each defect. The identification process is performed in order from the category written in the top row, and ends when identification conditions written in one row are all satisfied.

Such a logic table can be generated by a known method by using a database constructed by a learning process using, as teacher data, operation data in the past and results of specifying the category and degree of harmfulness of a defect by a checker on the basis of the operation data.

The defect detection unit 213 may specify the category and degree of harmfulness of a defect for each of the detected defect areas in this manner, and output the obtained specification results to the display control unit 205. Thus, information on a defect present on the surface of an inspection object to be inspected is output to a display unit (not illustrated). The defect detection unit 213 may also output the obtained specification results to an external device such as a process computer system for production management, and may create defect record files of products by utilizing the obtained specification results. Moreover, the defect detection unit 213 may contain information on the specification results of defect areas, as history information, in the storage unit 207 or the like, in association with time information on date and time at which the information is calculated.

The above description describes a case where the category and degree of harmfulness of a defect is identified by using a logic table, but a method for identifying the category and degree of harmfulness of a defect is not limited to the above example. For example, an identifier, such as neural network or a support vector machine (SVM), may be generated by a learning process using, as training data, operation data in the past and results of specifying the category and degree of harmfulness of a defect by a inspector on the basis of the operation data, and the identifier may be used for identifying the category and degree of harmfulness of a defect.

The configuration of the image processing unit 203 of the arithmetic processing apparatus 200 according to the present embodiment has been described.

An example of the function of the arithmetic processing apparatus 200 according to the present embodiment has been illustrated. Each of the above structural elements may be configured with a general-purpose member or circuit, and may be configured with hardware specialized for the function of each structural element. A CPU or the like may perform all of the functions of respective structural elements. Thus, a utilized configuration can be changed as appropriate, according to the technology level at the time of performing the present embodiment.

Note that the computer program for providing each function of the arithmetic processing apparatus according to the above present embodiment can be created and implemented in a personal computer or the like. Moreover, a computer-readable recording medium that contains this computer program can be provided as well. For example, the recording medium is a magnetic disk, an optical disc, a magneto-optical disk, a flash memory, or the like. The above computer program may be delivered via a network for example, without using the recording medium.

<Hardware Configuration>

Figure 15:
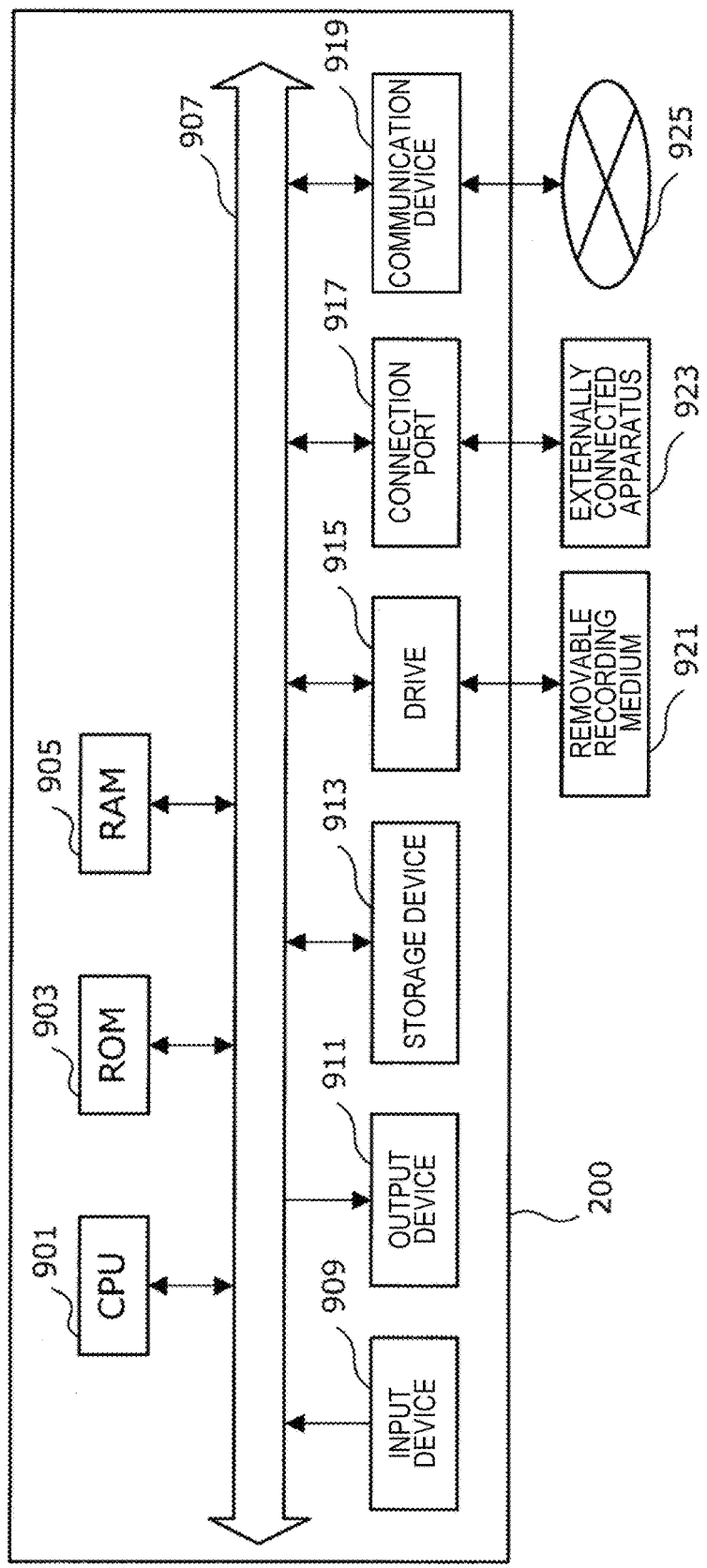
FIG. 15 is a block diagram illustrating the hardware configuration of an arithmetic processing apparatus according to the embodiment.

Next, the hardware configuration of the arithmetic processing apparatus 200 according to an embodiment of the present invention will be described in detail with reference to FIG. 15. FIG. 15 is a block diagram for explaining the hardware configuration of the arithmetic processing apparatus 200 according to an embodiment of the present invention.

The arithmetic processing apparatus 200 mainly includes a CPU 901, a ROM 903, and a RAM 905. Furthermore, the arithmetic processing apparatus 200 also includes a bus 907, an input device 909, an output device 911, a storage device 913, a drive 915, a connection port 917, and a communication device 919.

The CPU 901 serves as a central processing apparatus and a control device, and controls the overall operation or a part of the operation of the arithmetic processing apparatus 200 according to various programs recorded in the ROM 903, the RAM 905, the storage device 913, or a removable recording medium 921. The ROM 903 stores programs, operation parameters, and the like used by the CPU 901. The RAM 905 primarily stores programs that the CPU 901 uses and parameters and the like varying as appropriate during the execution of the programs. These are connected with each other via the bus 907 configured from an internal bus such as a CPU bus or the like.

The bus 907 is connected to the external bus such as a PCI (Peripheral Component Interconnect/Interface) bus via the bridge.

The input device 909 is an operation means operated by a user, such as a mouse, a keyboard, a touch panel, buttons, a switch and a lever. The input device 909 may be a remote control means (a so-called remote control) using, for example, infrared light or other radio waves, or may be an externally connected apparatus 923 such as a PDA conforming to the operation of the arithmetic processing apparatus 200. Furthermore, the input device 909 generates an input signal based on, for example, information which is input by a user with the above operation means, and is configured from an input control circuit for outputting the input signal to the CPU 901. The user can input various data to the arithmetic processing apparatus 200 and can instruct the arithmetic processing apparatus 200 to perform processing by operating this input device 909.

The output device 911 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 911 outputs a result obtained by various processes performed by the arithmetic processing apparatus 200. More specifically, the display device displays, in the form of texts or images, a result obtained by various processes performed by the arithmetic processing apparatus 200. On the other hand, the audio output device converts an audio signal such as reproduced audio data and sound data into an analog signal, and outputs the analog signal.

The storage device 913 is a device for storing data configured as an example of a storage unit of the arithmetic processing apparatus 200 and is used to store data. The storage device 913 is configured from, for example, a magnetic storage device such as a HDD (Hard Disk Drive), a semiconductor storage device, an optical storage device, or a magneto-optical storage device. This storage device 913 stores programs to be executed by the CPU 901, various data, and various data obtained from the outside.

The drive 915 is a reader/writer for recording medium, and is embedded in the arithmetic processing apparatus 200 or attached externally thereto. The drive 915 reads information recorded in the attached removable recording medium 921 such as a magnetic disk, an optical disk, a magneto-optical disk, or a semiconductor memory, and outputs the read information to the RAM 905. Furthermore, the drive 915 can write in the attached removable recording medium 921 such as a magnetic disk, an optical disk, a magneto-optical disk, or a semiconductor memory. The removable recording medium 921 is, for example, a CD medium, a DVD medium, or a Blu-ray (registered trademark) medium. The removable recording medium 921 may be a Compact-Flash (CF; registered trademark), a flash memory, an SD memory card (Secure Digital Memory Card), or the like. Alternatively, the removable recording medium 921 may be, for example, an IC card (Integrated Circuit Card) equipped with a non-contact IC chip or an electronic device.

The connection port 917 is a port for allowing devices to directly connect to the arithmetic processing apparatus 200. Examples of the connection port 917 include a USB (Universal Serial Bus) port, an IEEE1394 port, a SCSI (Small Computer System Interface) port, an RS-232C port, and the like. By the externally connected apparatus 923 connecting to this connection port 917, the arithmetic processing apparatus 200 directly obtains various data from the externally connected apparatus 923 and provides various data to the externally connected apparatus 923.

The communication device 919 is a communication interface configured from, for example, a communication device for connecting to a communication network 925. The communication device 919 is, for example, a wired or wireless LAN (Local Area Network), Bluetooth (registered trademark), a communication card for WUSB (Wireless USB), or the like. Alternatively, the communication device 919 may be a router for optical communication, a router for ADSL (Asymmetric Digital Subscriber Line), a modem for various communications, or the like. This communication device 919 can transmit and receive signals and the like in accordance with a predetermined protocol such as TCP/IP on the Internet and with other communication devices, for example. The communication network 925 connected to the communication device 919 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the arithmetic processing apparatus 200 according to an embodiment of the present invention has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

EXAMPLES

Example 1: Simulation Results of Inspection Object Imaging Apparatus

Figure 16:
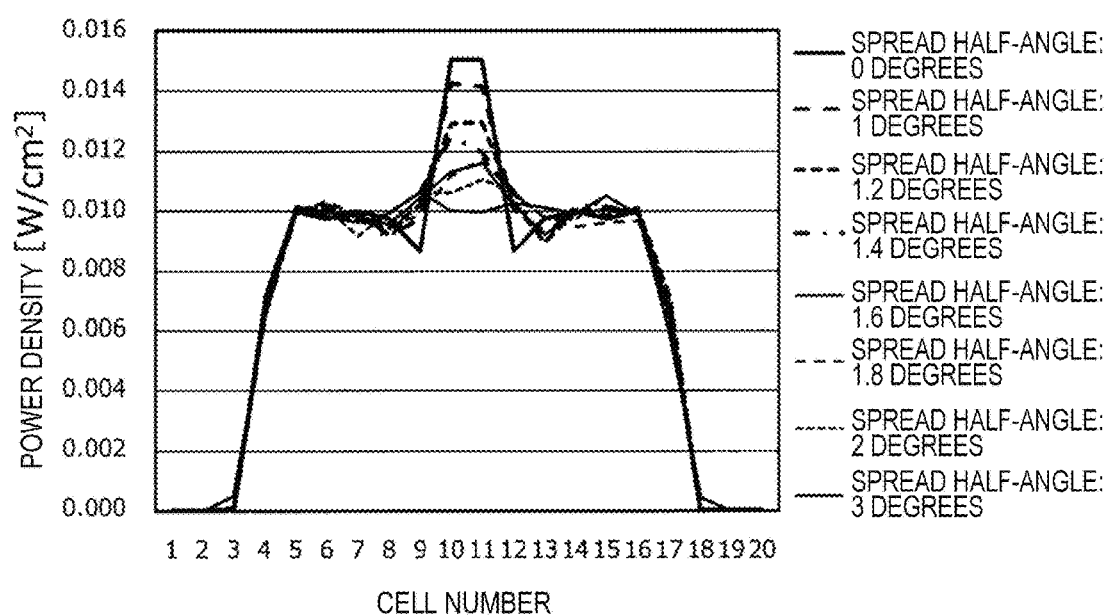
FIG. 16 is a graph diagram showing simulation results of an imaging unit according to the embodiment.
Figure 17:
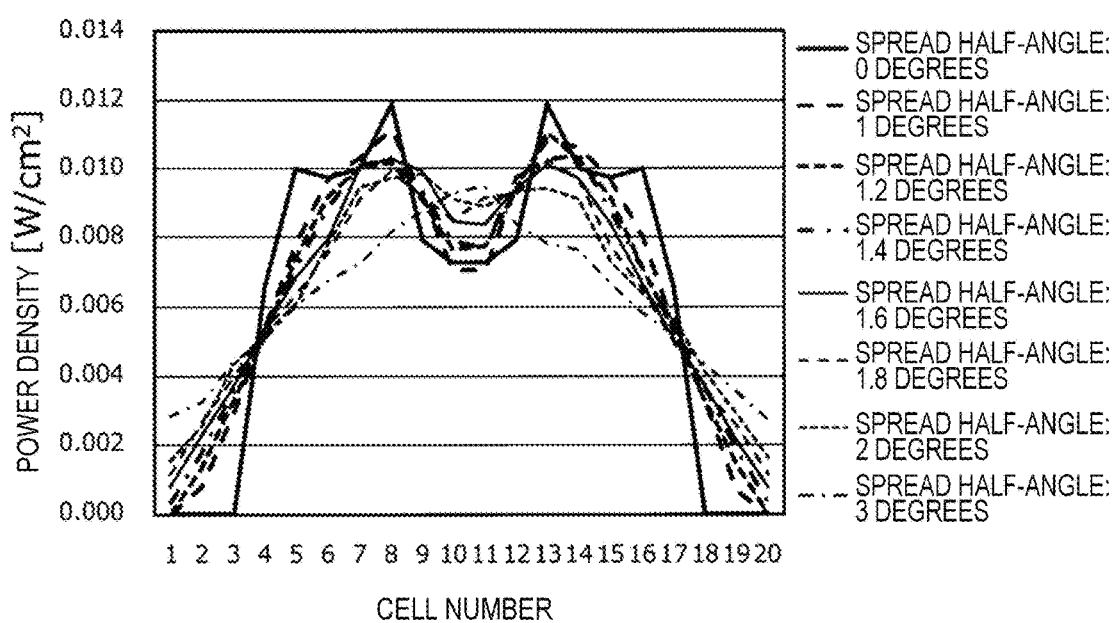
FIG. 17 is a graph diagram showing simulation results of an imaging unit according to the embodiment.

First, simulation results related to a spread half-angle of the light source 105 are specifically described, with reference to FIGS. 16 and 17.

In the present example, in the imaging unit illustrated in FIG. 8, the focal distance f1 of the convex lens 121 was set to 100 mm and the focal distance f2 of the convex lenses 127 and 129 was set to 50 mm, and ray tracing was performed for the following two cases: the shift amount Δ from the conjugate position=+20 mm, −20 mm.

In the ray tracing simulation, the spread half-angle of incident light was changed in a range from 0 degrees to 3 degrees, and computation was performed assuming that a spherical concavity with a diameter of 6 mm and a height of 5.1 μm was present at the center of the surface of an inspection object, which is a plane. On this occasion, a model was created on the assumption that a concave mirror with a focal distance of 500 mm and a diameter of 6 mm was embedded at the center of the plane. Here, the magnitude of an inclination corresponding to the concavity is $(5.1/3) \times 10^{-3}$ radians=0.1 degrees according to calculation by straight-line approximation.

Here, in the above simulation, 20×20=400 of 0.75 cm-square cells were assumed, 1000×1000 rays were arranged at equal intervals in the rectangle, and the rays were traced; thus, power densities on a sensor surface of an image sensor present at a position of (f2+Δ) were measured.

The obtained simulation results are shown in FIGS. 16 and 17. FIG. 16 shows the results for the shift amount Δ from the conjugate position=−20 mm, and FIG. 17 shows the results for the shift amount Δ from the conjugate position=+20 mm.

FIGS. 16 and 17 each show power density distribution when the sensor surface of the image sensor was sectioned at the center. Note that the obtained results were the same between a case where the sensor surface of the image sensor was sectioned in the depth direction of the page of FIG. 8 along the optical axis and a case where the sensor surface of the image sensor was sectioned in a direction parallel to the page of FIG. 8 along the optical axis. The number of the cells is an even number of 20×20; the two cells positioned at the center exhibited similar power density distribution.

In FIGS. 16 and 17, the vertical axis represents power density on the assumption that the total energy of rays is 1 W, and the horizontal axis represents cell number (i.e., the positions of the 20 cells).

According to FIGS. 16 and 17, first, it is found that power densities are distributed from cell number 4 to cell number 17 in both cases of Δ=−20 mm, +20 mm. This indicates that since the imaging unit illustrated in FIG. 8 is a telecentric optical system, even when the shift amount Δ from the conjugate position is changed, the size of an image on the sensor surface is the same between the positions of the two types of image sensors, which prevents a change in imaging resolution of pixels.

It is also found that, at Δ=−20 mm, power densities at cell numbers 9 to 12 are larger than power densities at surrounding cell numbers, and at Δ=+20 mm, power densities at cell numbers 9 to 12 are smaller than power densities at surrounding cell numbers. This indicates that the positions corresponding to cell numbers 9 to 12 at Δ=−20 mm are brighter than the surroundings, and the positions corresponding to cell numbers 9 to 12 at Δ=+20 mm are darker than the surroundings.

Here, when the magnitude of the spread half-angle is increased from 0 degrees, power densities at cell numbers 9 to 12 gradually decrease in the results of FIG. 16, and power densities at cell numbers 9 to 12 gradually increase in the results of FIG. 17.

It is also found that in FIG. 16, when the magnitude of the spread half-angle exceeds 2 degrees (i.e., the magnitude of the spread half-angle exceeds 20 times the inclination of 0.1 degrees), power densities at cell numbers 9 to 12 become substantially the same as power densities of surrounding cells. Similarly, in FIG. 17, when the magnitude of the spread half-angle is in a range of 0 degrees to 2 degrees, a shape having a valley around cell numbers 9 to 12 and two peaks on both sides of this valley is exhibited, but when the magnitude of the spread half-angle exceeds 2 degrees, two peaks are no longer present, and an appearance that is different from the shape when the magnitude of the spread half-angle is in a range of 0 degrees to 2 degrees is exhibited. These results indicate that when the magnitude of the spread half-angle exceeds 20 times the magnitude of inclination, light and dark due to the concavity become unclear.

Example 2: Simulation Results of Inspection Object Imaging Apparatus

Figure 18A:
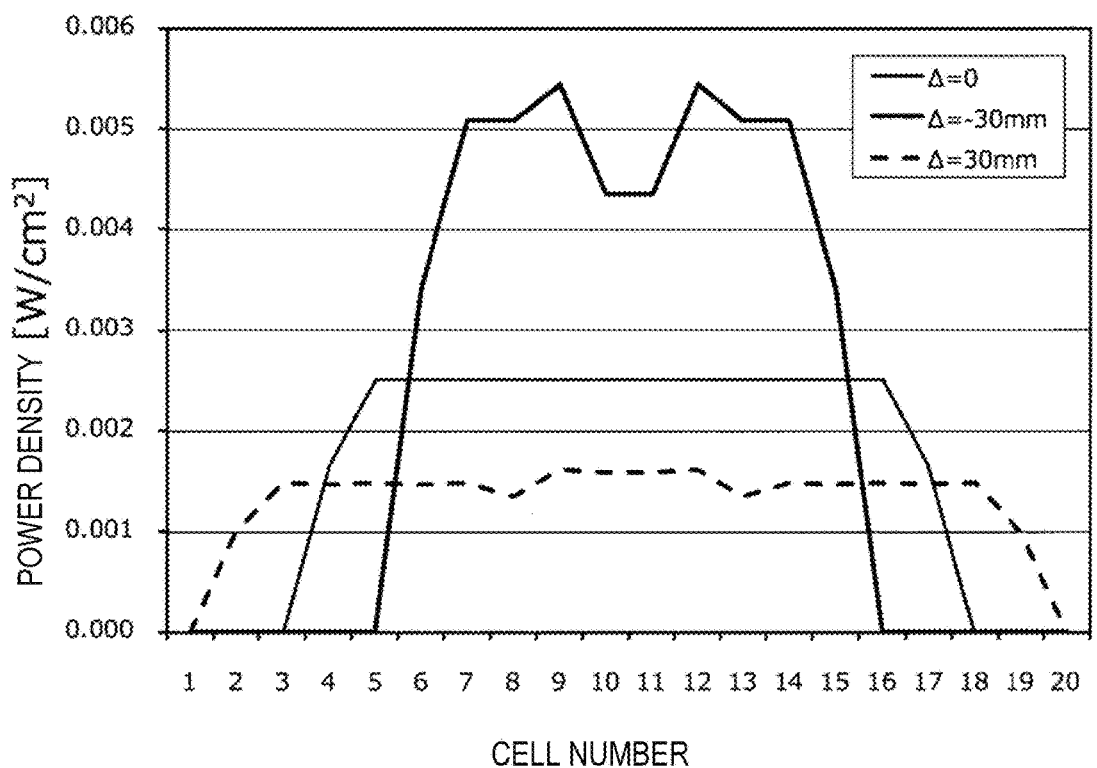
FIG. 18A is a graph diagram showing simulation results of an imaging unit according to the embodiment.
Figure 18B:
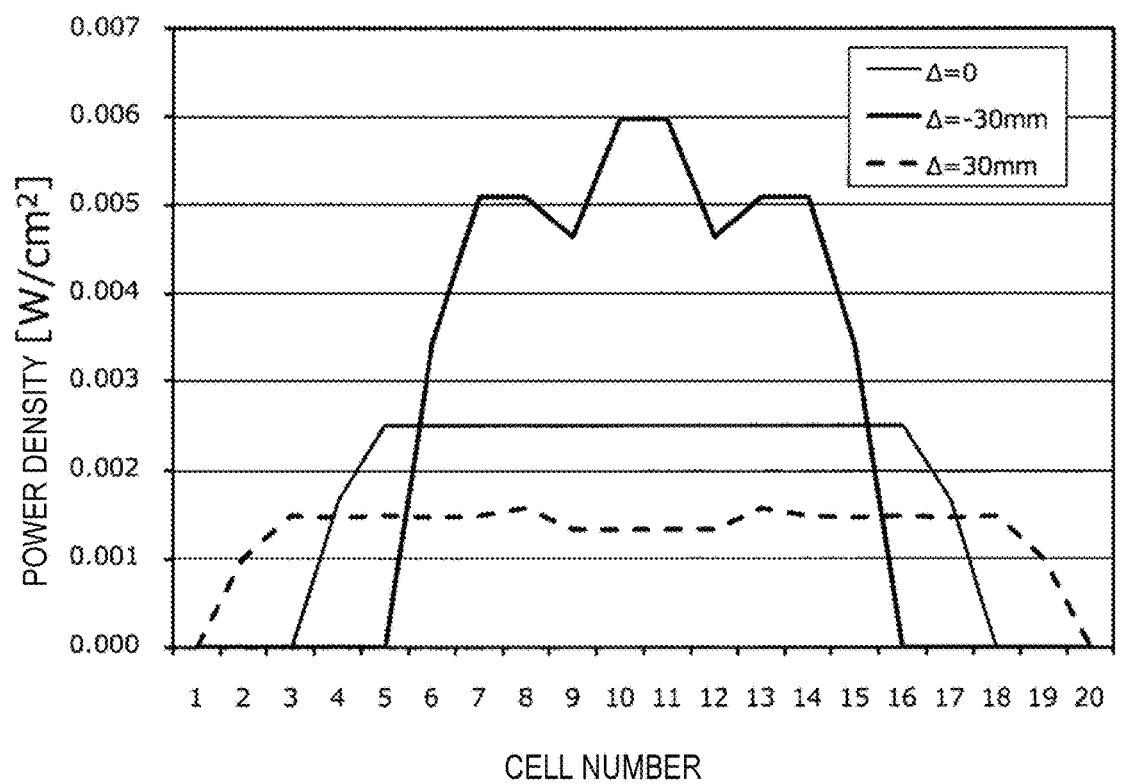
FIG. 18B is a graph diagram showing simulation results of an imaging unit according to the embodiment.

Next, simulation results of an inspection object imaging apparatus including the imaging unit with one convex lens illustrated in FIG. 7 are specifically described, with reference to FIGS. 18A and 18B.

In the present example, in the imaging unit illustrated in FIG. 7, the separation distance L1 was set to 200 mm, the separation distance L2 was set to 200 mm, and the focal distance f1 of the convex lens 121 was set to 100 mm, and ray tracing was performed for the following three cases: the shift amount Δ from the conjugate position=+30 mm, 0 mm, −30 mm.

In the ray tracing simulation, assuming that incident light is parallel light with a spread half-angle of zero, computation was performed for the following two cases: (i) a case where a spherical concavity with a diameter of 6 mm and a depth of 4.5 μm is present, and (ii) a case where a spherical convexity with a diameter of 6 mm and a height of 4.5 μm is present, at the center of the surface of an inspection object, which is a plane. On this occasion, each model was created on the assumption that a concave mirror or a convex mirror with a focal distance of 500 mm and a diameter of 6 mm was embedded at the center of the plane.

Here, in each simulation, 20×20=400 of 1.5 cm-square cells were assumed, 1000×1000 rays were arranged at equal intervals in the rectangle, and the rays were traced; thus, power densities on a sensor surface of an image sensor present at a position of (L2+Δ) were measured.

FIG. 18A shows simulation results for the case where the concavity is present, and FIG. 18B shows simulation results for the case where the convexity is present. Here, FIGS. 18A and 18B each show power density distribution when the sensor surface of the image sensor was sectioned at the center. Note that the obtained results were the same between a case where the sensor surface of the image sensor was sectioned in the depth direction of the page of FIG. 7 along the optical axis and a case where the sensor surface of the image sensor was sectioned in a direction parallel to the page of FIG. 7 along the optical axis. The number of the cells is an even number of 20×20; the two cells positioned at the center exhibited similar power density distribution.

In FIGS. 18A and 18B, the vertical axis represents power density on the assumption that the total energy of rays is 1 W, and the horizontal axis represents cell number (i.e., the positions of the 20 cells).

First, as a phenomenon common to FIGS. 18A and 18B, power densities are distributed from cell number 5 to cell number 16 at $\Delta=-30$ mm, whereas power densities are distributed from cell number 3 to cell number 18 at $\Delta=0$ mm (i.e., the conjugate position), and from cell number 1 to cell number 20 at $\Delta=+30$ mm. This indicates that since a case where only one convex lens is present as the imaging optical system is assumed, the size of an image on the sensor surface is different between the positions of the three types of image sensors.

Moreover, according to power density distribution at $\Delta=0$ mm, it is found that power density is constant in both of FIGS. 18A and 18B. This indicates that at the conjugate position, the concavity or convexity assumed on the surface of the inspection object is not visualized as a difference between light and dark.

In addition, according to FIG. 18A showing the results when a concavity is present, it is found that at $\Delta=-30$ mm, power densities at cell numbers 10 to 11 are smaller than power densities at surrounding cell numbers, and at $\Delta=+30$ mm, power densities at cell numbers 9 to 12 are larger than power densities at surrounding cell numbers. This indicates that the positions corresponding to cell numbers 10 to 11 at $\Delta=-30$ mm are darker than the surroundings, and the positions corresponding to cell numbers 9 to 12 at $\Delta=+30$ mm are brighter than the surroundings.

Thus, in the case where a concavity is present on the surface of an inspection object, a portion corresponding to the concavity is observed as a dark portion at $\Delta=-30$ mm, and a portion corresponding to the concavity is observed as a bright portion at $\Delta=+30$ mm.

On the other hand, according to FIG. 18B showing the results when a convexity is present, it is found that at $\Delta=-30$ mm, power densities at cell numbers 10 to 11 are larger than power densities at surrounding cell numbers, and at $\Delta=+30$ mm, power densities at cell numbers 9 to 12 are smaller than power densities at surrounding cell numbers. This indicates that the positions corresponding to cell numbers 10 to 11 at $\Delta=-30$ mm are brighter than the surroundings, and the positions corresponding to cell numbers 9 to 12 at $\Delta=+30$ mm are darker than the surroundings.

Thus, in the case where a convexity is present on the surface of an inspection object, a portion corresponding to the convexity is observed as a bright portion at $\Delta=-30$ mm, and a portion corresponding to the convexity is observed as a dark portion at $\Delta=+30$ mm.

Example 3: Simulation Results of Inspection Object Imaging Apparatus

Figure 19:
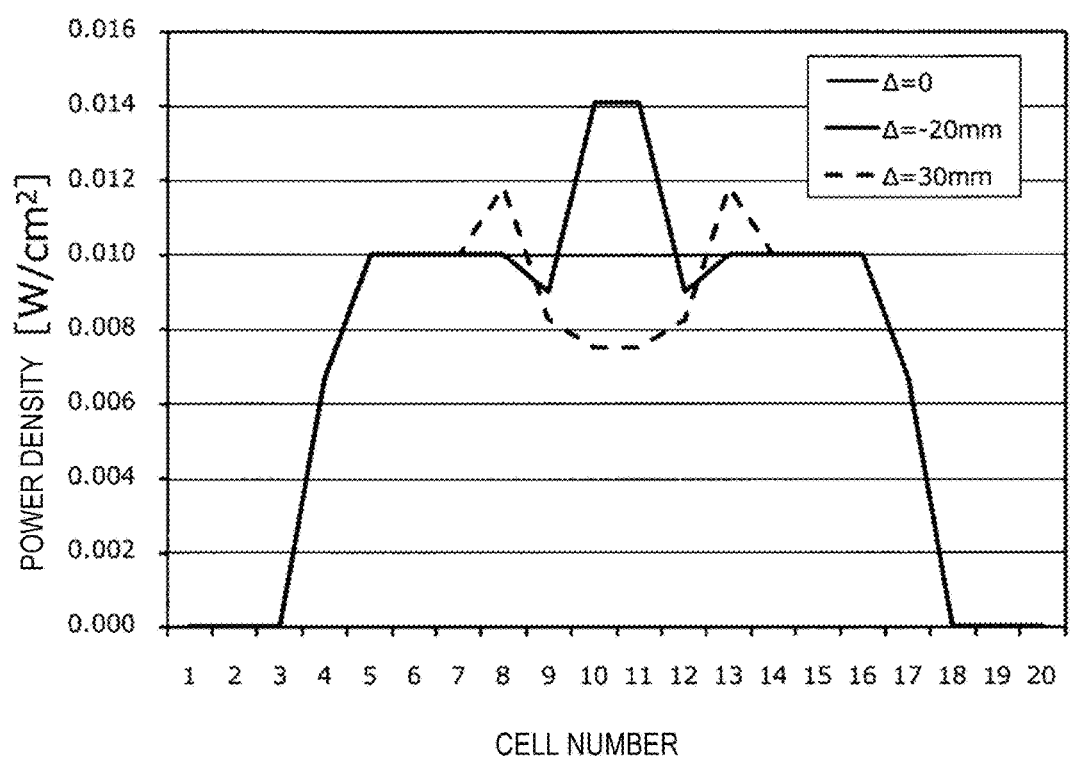
FIG. 19 is a graph diagram showing simulation results of an imaging unit according to the embodiment.

Next, simulation results of an inspection object imaging apparatus including the imaging unit with two convex lenses illustrated in FIG. 8 are specifically described, with reference to FIG. 19.

In the present example, in the imaging unit illustrated in FIG. 8, the focal distance f1 of the convex lens 121 was set to 100 mm and the focal distance f2 of the convex lenses 127 and 129 was set to 50 mm, and ray tracing was performed for the following three cases: the shift amount $\Delta$ from the conjugate position=+30 mm, 0 mm, −20 mm.

In the ray tracing simulation, assuming that incident light is parallel light with a spread half-angle of zero, computation was performed on the assumption that a spherical convexity with a diameter of 6 mm and a height of 4.5 μm was present at the center of the surface of an inspection object, which is a plane. On this occasion, a model was created on the assumption that a convex mirror with a focal distance of 500 mm and a diameter of 6 mm was embedded at the center of the plane.

Here, in the above simulation, 20×20=400 of 0.75 cm-square cells were assumed, 1000×1000 rays were arranged at equal intervals in the rectangle, and the rays were traced; thus, power densities on a sensor surface of an image sensor present at a position of (f2+$\Delta$) were measured.

The obtained simulation results are shown in FIG. 19. FIG. 19 shows power density distribution when the sensor surface of the image sensor was sectioned at the center. Note that the obtained results were the same between a case where the sensor surface of the image sensor was sectioned in the depth direction of the page of FIG. 8 along the optical axis and a case where the sensor surface of the image sensor was sectioned in a direction parallel to the page of FIG. 8 along the optical axis. The number of the cells is an even number of 20×20; the two cells positioned at the center exhibited similar density distribution of the number of rays.

In FIG. 19, the vertical axis represents power density on the assumption that the total energy of rays is 1 W, and the horizontal axis represents cell number (i.e., the positions of the 20 cells).

According to FIG. 19, first, it is found that power densities are distributed from cell number 3 to cell number 18 in all cases of $\Delta=-20$ mm, 0 mm, +30 mm. This indicates that since the imaging unit illustrated in FIG. 8 is a telecentric optical system, even when the shift amount $\Delta$ from the conjugate position is changed, the size of an image on the sensor surface is the same between the positions of the three types of image sensors, which prevents a change in imaging resolution of pixels.

Moreover, according to power density distribution at $\Delta=0$ mm, it is found that power density is constant regardless of the positions of cells. This indicates that at the conjugate position, the convexity assumed on the surface of the inspection object is not visualized as a difference between light and dark.

It is also found that, at $\Delta=-20$ mm, power densities at cell numbers 9 to 12 are larger than power densities at surrounding cell numbers, and at $\Delta=+30$ mm, power densities at cell numbers 9 to 12 are smaller than power densities at surrounding cell numbers. This indicates that the positions corresponding to cell numbers 9 to 12 at $\Delta=-20$ mm are brighter than the surroundings, and the positions corresponding to cell numbers 9 to 12 at $\Delta=+30$ mm are darker than the surroundings. It is also found that the behavior of a bright portion occurring in the case where the image sensor is placed on the inspection object side with respect to the conjugate position (i.e., the side on which the value of $\Delta$ is negative), and a dark portion occurring in the case where the image sensor is placed further on the travel direction side with respect to the conjugate position (i.e., the side on which the value of $\Delta$ is positive) is similar to the simulation results shown in FIG. 18B.

Example 4: Imaging Results of Steel Sheet

Next, description is given on captured images obtained by imaging an actual metal plate by using an inspection object imaging apparatus including the imaging unit with two convex lenses illustrated in FIG. 8.

In the present example, a quantum cascade laser light source without an external resonator having a center wavelength of 10 μm, a spectral bandwidth of 400 nm, and a spread half-angle of 0.1 milliradians was used as the light source 105, and infrared light emitted from the light source was made into parallel infrared light. Note that the magnitude of the spread half-angle was 20 times or less the minimum inclination of a surface, which is defined as detection resolution. In the imaging unit illustrated in FIG. 8, a telecentric optical system in which the focal distance f1 of the convex lens 121 was set to 500 mm and the focal distance f2 of the convex lenses 127 and 129 was set to 35 mm was used, image sensors were installed at two positions with shift amounts from the conjugate position of Δ=+3 mm and Δ=−3 mm, and the actual metal plate was imaged. Note that the shift amounts of Δ=+3 mm satisfy the relation expressed by the above formula (134).

At the center of the steel sheet to be imaged, a convex flaw with a diameter of 4 mm and a height of 3 μm was present.

The obtained results are shown in FIG. 20.

It is apparent from FIG. 20 that in both cases of Δ=−3 mm and Δ=+3 mm, the convex flaw present at the center portion appears white at Δ=−3 mm, and appears black at Δ=+3 mm. In the captured images shown in FIG. 20, the portion that appears white corresponds to a portion with high luminance, and the portion that appears black corresponds to a portion with low luminance.

It is apparent from comparison to the simulation results shown in FIG. 19 that the behavior of a bright portion occurring in the case where the image sensor is placed on the inspection object side with respect to the conjugate position (i.e., the side on which the value of Δ is negative), and a dark portion occurring in the case where the image sensor is placed further on the travel direction side with respect to the conjugate position (i.e., the side on which the value of Δ is positive) is a behavior when a convexity is present on the surface of an inspection object. Accordingly, by using the captured images shown in FIG. 20, it is possible to identify that an unevenness flaw is actually a convex flaw according to a combination of light and dark.

The preferred embodiment(s) of the present invention has/have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST 10 surface inspection apparatus
100 inspection object imaging apparatus
101 light beam projecting unit
103 imaging unit
105 light source
107 projection optical system
109 imaging optical system
111, 113 infrared camera
121, 127, 129 convex lens
123, 125 image sensor
200 arithmetic processing apparatus
201 imaging control unit
203 image processing unit
205 display control unit
207 storage unit
211 A/D conversion unit
213 defect detection unit
BS beam splitter
S inspection object

The invention claimed is:

1. An inspection object imaging apparatus comprising:
   a light source configured to produce a light beam belonging to an infrared wavelength band, a spread half-angle of the light beam on a surface of an inspection object being 20 times or less a minimum inclination of a surface to be imaged;
   a projection optical system configured to project the light beam on the surface of the inspection object at a predetermined projection angle; and
   an imaging unit configured to image the light beam reflected at the surface of the inspection object,
   wherein the imaging unit includes
      an imaging optical system including at least one convex lens, configured to condense reflected light from the surface of the inspection object, and including a branching optical element that branches the reflected light to two different directions, and
      a first image sensor and a second image sensor each configured to image the reflected light that has passed through the imaging optical system,
      wherein the first image sensor is provided on the inspection object side with respect to a position of the imaging optical system that is conjugate with the surface of the inspection object, along an optical axis of the reflected light, and
      the second image sensor is provided on the reflected-light travel direction side with respect to the conjugate position of the imaging optical system, along an optical axis of the reflected light,
   wherein for each of the first image sensor and the second image sensor, a shift amount Δ [mm] from the conjugate position is set to satisfy a condition expressed by Formula (1) below, where ß is a lateral magnification of the imaging optical system, p [mm] is a pixel pitch in each image sensor, and T is a minimum value of an inclination to be imaged on the surface,

[Math. 1]

$$\Delta > \frac{p \cdot \beta}{T}. \quad \text{Formula (1)}$$

2. The inspection object imaging apparatus according to claim 1,
   wherein the imaging optical system further includes
      a first condensing optical system provided between the branching optical element and the first image sensor, and configured to condense the reflected light onto the first image sensor, and
      a second condensing optical system provided between the branching optical element and the second image sensor, and configured to condense the reflected light onto the second image sensor.

3. The inspection object imaging apparatus according to claim 1, wherein the light beam produced by the light source is parallel light.

4. The inspection object imaging apparatus according to claim 1,
wherein the light source is a quantum cascade laser without an external resonator.

5. The inspection object imaging apparatus according to claim 1,
wherein the inspection object is positioned on a surface of a roll having a predetermined curvature, and
the projection optical system and the imaging optical system include a cylindrical lens whose focus coincides with a rotation center axis of the roll.

6. The inspection object imaging apparatus according to claim 1,
wherein the first image sensor and the second image sensor are provided to be inclined with respect to an optical axis so that a shift amount from the conjugate position at pixel positions in each image sensor is constant.

7. An inspection object imaging method comprising:
projecting, from a light source configured to produce a light beam belonging to an infrared wavelength band, a spread half-angle of the light beam on a surface of an inspection object being 20 times or less a minimum inclination of a surface to be imaged, the light beam on the surface of the inspection object at a predetermined projection angle via a projection optical system;
condensing reflected light that is the light beam reflected at the surface of the inspection object using an imaging optical system including at least one convex lens, and branching the reflected light to two different directions by a branching optical element included in the imaging optical system; and
imaging the reflected light that has formed an image in a first image sensor, by the first image sensor provided on the inspection object side with respect to a position of the imaging optical system that is conjugate with the surface of the inspection object, along an optical axis of the reflected light, and imaging the reflected light that has formed an image in a second image sensor, by the second image sensor provided on the reflected-light travel direction side with respect to the conjugate position of the imaging optical system, along an optical axis of the reflected light,
wherein for each of the first image sensor and the second image sensor, a shift amount Δ [mm] from the conjugate position is set to satisfy a condition expressed by Formula (1) below, where β is a lateral magnification of the imaging optical system, p [mm] is a pixel pitch in each image sensor, and T is a minimum value of an inclination to be imaged on the surface,

[Math. 2]

$$\Delta > \frac{p \cdot \beta}{T}. \quad \text{Formula (1)}$$

8. The inspection object imaging method according to claim 7,
wherein the imaging optical system further includes
a first condensing optical system provided between the branching optical element and the first image sensor, and configured to condense the reflected light onto the first image sensor, and
a second condensing optical system provided between the branching optical element and the second image sensor, and configured to condense the reflected light onto the second image sensor.

9. The inspection object imaging method according to claim 7,
wherein the light beam produced by the light source is parallel light.

10. The inspection object imaging method according to claim 7,
wherein the light source is a quantum cascade laser without an external resonator.

11. The inspection object imaging method according to claim 7,
wherein the inspection object is positioned on a surface of a roll having a predetermined curvature, and
the projection optical system and the imaging optical system include a cylindrical lens whose focus coincides with a rotation center axis of the roll.

12. The inspection object imaging method according to claim 7,
wherein the first image sensor and the second image sensor are provided to be inclined with respect to an optical axis so that a shift amount from the conjugate position at pixel positions in each image sensor is constant.

13. A surface inspection apparatus comprising:
an inspection object imaging apparatus that projects a light beam belonging to an infrared wavelength band on a surface of an inspection object at a predetermined projection angle, and images reflected light from the surface of the inspection object; and
an arithmetic processing apparatus that performs image processing on captured images of the reflected light captured by the inspection object imaging apparatus, and detects a surface defect present on the surface of the inspection object,
the inspection object imaging apparatus including
a light source configured to produce a light beam belonging to an infrared wavelength band, a spread half-angle of the light beam on a surface of an inspection object being 20 times or less a minimum inclination of a surface to be imaged,
a projection optical system configured to project the light beam on the surface of the inspection object at a predetermined projection angle, and
an imaging unit configured to image the light beam reflected at the surface of the inspection object,
wherein the imaging unit includes
an imaging optical system including at least one convex lens, configured to condense reflected light from the surface of the inspection object, and including a branching optical element that branches the reflected light to two different directions, and
a first image sensor and a second image sensor each configured to image the reflected light that has passed through the imaging optical system,
wherein the first image sensor is provided on the inspection object side with respect to a position of the imaging optical system that is conjugate with the surface of the inspection object, along an optical axis of the reflected light, and
the second image sensor is provided on the reflected-light travel direction side with respect to the conjugate position of the imaging optical system, along an optical axis of the reflected light, and wherein, on the basis of distribution of light and dark of a first captured image captured by the first image sensor and a second captured image captured by the second image sensor, the arithmetic processing apparatus detects a portion where light and dark are reversed between the first captured image and the second captured image, as unevenness present on the surface of the inspection object, wherein for each of the first image sensor and the second image sensor, a shift amount Δ [mm] from the conjugate position is set to satisfy a condition expressed by Formula (1) below, where β is a lateral magnification of the imaging optical system, p [mm] is a pixel pitch in each image sensor, and T is a minimum value of an inclination to be detected on the surface,

[Math. 3]

$$\Delta > \frac{p \cdot \beta}{T}. \quad \text{Formula (1)}$$

14. The surface inspection apparatus according to claim 13, wherein the imaging optical system further includes
a first condensing optical system provided between the branching optical element and the first image sensor, and configured to condense the reflected light onto the first image sensor, and
a second condensing optical system provided between the branching optical element and the second image sensor, and configured to condense the reflected light onto the second image sensor.

15. The surface inspection apparatus according to claim 13, wherein the light beam produced by the light source is parallel light.

16. The surface inspection apparatus according to claim 13, wherein the light source is a quantum cascade laser without an external resonator.

17. The surface inspection apparatus according to claim 13, wherein the inspection object is positioned on a surface of a roll having a predetermined curvature, and
the projection optical system and the imaging optical system include a cylindrical lens whose focus coincides with a rotation center axis of the roll.

18. The surface inspection apparatus according to claim 13, wherein the first image sensor and the second image sensor are provided to be inclined with respect to an optical axis so that a shift amount from the conjugate position at pixel positions in each image sensor is constant.

19. A surface inspection method comprising:
a step of
projecting, from a light source configured to produce a light beam belonging to an infrared wavelength band, a spread half-angle of the light beam on a surface of an inspection object being 20 times or less a minimum inclination of a surface to be imaged, the light beam on the surface of the inspection object at a predetermined projection angle via a projection optical system,
condensing reflected light that is the light beam reflected at the surface of the inspection object using an imaging optical system including at least one convex lens, and branching the reflected light to two different directions by a branching optical element included in the imaging optical system, and
imaging the reflected light that has formed an image in a first image sensor, by the first image sensor provided on the inspection object side with respect to a position of the imaging optical system that is conjugate with the surface of the inspection object, along an optical axis of the reflected light, and imaging the reflected light that has formed an image in a second image sensor, by the second image sensor provided on the reflected-light travel direction side with respect to the conjugate position of the imaging optical system, along an optical axis of the reflected light; and
a step of, on the basis of distribution of light and dark of a first captured image captured by the first image sensor and a second captured image captured by the second image sensor, detecting a portion where light and dark are reversed between the first captured image and the second captured image, as unevenness present on the surface of the inspection object,
wherein for each of the first image sensor and the second image sensor, a shift amount Δ [mm] from the conjugate position is set to satisfy a condition expressed by Formula (1) below, where β is a lateral magnification of the imaging optical system, p [mm] is a pixel pitch in each image sensor, and T is a minimum value of an inclination to be detected on the surface,

[Math. 4]

$$\Delta > \frac{p \cdot \beta}{T}. \quad \text{Formula (1)}$$

20. The surface inspection method according to claim 19, wherein the imaging optical system further includes
a first condensing optical system provided between the branching optical element and the first image sensor, and configured to condense the reflected light onto the first image sensor, and
a second condensing optical system provided between the branching optical element and the second image sensor, and configured to condense the reflected light onto the second image sensor.

21. The surface inspection method according to claim 19, wherein the light beam produced by the light source is parallel light.

22. The surface inspection method according to claim 19, wherein the light source is a quantum cascade laser without an external resonator.

23. The surface inspection method according to claim 19, wherein the inspection object is positioned on a surface of a roll having a predetermined curvature, and
the projection optical system and the imaging optical system include a cylindrical lens whose focus coincides with a rotation center axis of the roll.

24. The surface inspection method according to claim 19, wherein the first image sensor and the second image sensor are provided to be inclined with respect to an optical axis so that a shift amount from the conjugate position at pixel positions in each image sensor is constant.

* * * * *